US008158578B2

(12) United States Patent
Reid et al.

(10) Patent No.: US 8,158,578 B2
(45) Date of Patent: *Apr. 17, 2012

(54) METHODS FOR TREATING NEUROLOGICAL DEFICITS

(75) Inventors: James Steven Reid, Berkeley, CA (US); James H. Fallon, Irvine, CA (US)

(73) Assignee: Neurorepair, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/869,468

(22) Filed: Aug. 26, 2010
(Under 37 CFR 1.47)

(65) Prior Publication Data

US 2011/0071078 A1  Mar. 24, 2011

Related U.S. Application Data

(63) Continuation of application No. 09/129,028, filed on Aug. 4, 1998, now Pat. No. 7,790,669.

(60) Provisional application No. 60/055,383, filed on Aug. 4, 1997.

(51) Int. Cl.
| *A61K 38/00* | (2006.01) |
| *A61K 49/00* | (2006.01) |
| *A61K 38/18* | (2006.01) |
| *A61B 5/00* | (2006.01) |
| *C07K 14/475* | (2006.01) |
| *C07K 14/48* | (2006.01) |

(52) U.S. Cl. ............ 514/1.1; 514/1.2; 514/1.3; 514/7.6; 514/8.3; 514/8.4

(58) Field of Classification Search .................. None
See application file for complete search history.

(56) References Cited

U.S. PATENT DOCUMENTS

| 4,816,561 A | 3/1989 | Todaro |
| 4,863,899 A | 9/1989 | Todaro |
| 4,863,902 A | 9/1989 | Amagase et al. |
| 5,026,381 A | 6/1991 | Li |
| 5,240,912 A | 8/1993 | Todaro |
| 5,342,777 A | 8/1994 | Cole et al. |
| 5,411,883 A | 5/1995 | Boss et al. |
| 5,750,376 A | 5/1998 | Weiss et al. |
| 5,756,457 A | 5/1998 | Wang et al. |
| 5,800,812 A | 9/1998 | Eisenbach-Schwartz et al. |
| 5,851,832 A | 12/1998 | Weiss et al. |
| 5,942,487 A | 8/1999 | Ogawa et al. |
| 5,980,885 A | 11/1999 | Weiss et al. |
| 5,981,165 A | 11/1999 | Weiss et al. |
| 6,071,889 A | 6/2000 | Weiss et al. |
| 6,093,531 A | 7/2000 | Bjornson et al. |
| 6,486,122 B1 | 11/2002 | Twardzik et al. |
| 6,677,307 B2 | 1/2004 | Twardzik et al. |
| 6,764,683 B1 | 7/2004 | Twardzik et al. |
| 6,815,418 B2 | 11/2004 | Twardzik et al. |
| 7,329,645 B2 | 2/2008 | Twardzik et al. |
| 7,365,172 B2 | 4/2008 | Twardzik et al. |
| 7,790,669 B1 * | 9/2010 | Reid et al. ............ 514/8.9 |
| 7,795,202 B2 * | 9/2010 | Fallon et al. .......... 514/8.9 |
| 2002/0193301 A1 | 12/2002 | Twardzik et al. |
| 2008/0242611 A1 | 10/2008 | Twardzik et al. |
| 2009/0068139 A1 | 3/2009 | Twardzik et al. |

FOREIGN PATENT DOCUMENTS

| WO | WO 93/01275 | 1/1993 |
| WO | WO 94/16718 | 8/1994 |
| WO | WO 98/22127 | 5/1998 |
| WO | WO 99/06060 | 2/1999 |
| WO | WO 00/65028 | 11/2000 |
| WO | WO 01/12127 | 2/2001 |

OTHER PUBLICATIONS

Abboud, et al., "Insulin Effects on Differentiation of Fetal Neuron Cell Cultures," Soc . Neurosci. Abstr. 23 : 1425, 1997.
"Adult stem cells activated in mammalian brain", today.uci.edu/news/release_detail.asp?key=1801, Jul. 24, 2008.
Ahmed S., et al., "BDNF Enhances the Differentiation but not the Survival of CNS Stem Cell-Derived Neuronal Precursors" Journal of Neuroscience, New York, NY, US vol. 15, No. 8, Aug. 1, 1995 pp. 5765-5778.
Alexi T., et al., "Protective Effects of Neurotrophin-4/5 And Transforming Growth Factor-α On Striatal Neuronal Phenotypic Degeneration After Excitotoxic Lesioning With Quinolinic Acid" (1997) Neuroscience 78(1):73-86.
Alexi T., et al.,"Trophic Actions of Transforming Growth Factor A On Mesencephalic Dopaminergic Neurons Developing In Culture" (1993) Neuroscience 55(4):903-918.
Alheid, et al., "Theories of basal forebrain organization and the "emotional motor system"," Progr. Brain Res. 107:461-484, 1996.
Anchan et al., "EGF and TGF-α Stimulate Retinal Neuroepithelial Cell Proliferation In Vitro," Neuron, 6: 923-936 (1991).
Andersson, et al., "Differential Expression of Fgfri—R4 In The Rat Nervous System", Dept. Cell Biology & Anatomy, Oregon Health Services University, Portland, OR 97201, Society for Neuroscience Abstracts vol. 20, 1994, p. 40.
Babic, et al., "CYR61, a product of a growth factor-inducible immediate early gene, promotes angiogenesis and tumor growth," Proc. NatL Acad. Sci. USA, 95:6355, 1998. Barnard, et al., "Auto- and Cross-induction within the Mammalian Epidermal Growth Factor-related Peptide Family," J. Biol. Chem. 269 : 22817-22822, 1994.
Bayer S., "Neurogenesis in the Rat Neostriatum," Intl. J. Devel. Neurosci. 2 : 163-175, 1984.

(Continued)

*Primary Examiner* — Chang-Yu Wang
(74) *Attorney, Agent, or Firm* — Ropes & Gray LLP; James F. Haley, Jr.; Yang Xu

(57) ABSTRACT

The present invention features methods and compositions for treating a patient who has a neurological deficit. The method can be carried out, for example, by contacting (in vivo or in culture) a neural progenitor cell of the patient's central nervous system (CNS) with a polypeptide that binds the epidermal growth factor (EGF) receptor and directing progeny of the proliferating progenitor cells to migrate en masse to a region of the CNS in which they will reside and function in a manner sufficient to reduce the neurological deficit. The method may include a further step in which the progeny of the neural precursor cells are contacted with a compound that stimulates differentiation.

7 Claims, 12 Drawing Sheets

OTHER PUBLICATIONS

Bayer, et al., "Directions in Neurogenetic Gradients and Patterns of Anatomical Connections in the Telencephalon," Prog. Neurobiol. 29 : 57-106, 1987.

Beerli, et al., "Epidermal Growth Factor-related Peptides activate Distinct Subsets of ErbB Receptors and Differ in Their Biological Activities," J. of Biol. Chem., 271(11):6071-6076, Mar. 15, 1996.

Blomquist, et al., "Vaccinia virus 19-kilodalton protein: Relationship to several mammalian proteins, including two growth factors," Proc. Natl. Acad. Sci. USA 81 : 7363-7367, 1984.

Book by William Broad and Nicholas Wade, "Betrayers of the Truth", Simon and Schuster, p. 54 (1982).

Boonstra, et al., 1995 Cell Biology Int'l 19(5):413-430.

Borgundvaag, et al., "Dopamine receptor activation inhibits estrogen-stimulated transforming growth factor-alpha gene expression and growth in anterior pituitary, but not in uterus," Endocrinol. 130 : 3453-3458, 1992

Brazelton, T., "From Marrow to Brain: Expression of Neuronal Phenotypes in Adult Mice,"(2000) Science 290:1775.

Burgess, et al., "Possible Dissociation of Heparin-binding and Mitogenic Activities of Heparin-binding (Acidic Fibroblast) Growth Factor-1 from Its Receptor-binding Activities by Site-directed Mutagenesis of a Single Lysine Residue", J of Cell Bio. 1990, 111:2129-2138.

Carpenter, et al., "Antibodies to the epidermal growth factor receptor block the biological activities of sarcoma growth factor", PNAS 80(18):5627-30, 1983.

Casper, et al., "EGF Enhances the Survival of Dopamine Neurons in Rat Embryonic Mesencephalon Primary Cell Culture," J. Neurosci. Res. 30:372-381, 1991.

Casper, et al., "Epidermal Growth Factor and Basic Fibroblast Growth Factor Protect Dopaminergic Neurons from Glutamate Toxicity in Culture," J. Neurochem. 65:1016-1026, 1995.

Catapano, et al., "Human Fetal Precursor Cells are Capable of Survival, Neuronal Differentiation, and Integration Following Transplantation into Neonatal Rat Brain," Soc. Neurosci. Abstr. 23 : 345, 1997.

Centers for Disease Control and Prevention, www.cdc.gov , Stroke Fact, Feb. 28, 2011.

Chalazonitis A. et al., Transforming Growth Factor , But Not Epidermal Growth Factor, Promotes the Survival of Sensory Neurons In Vitro in Vitro 1992 Journal of Neuroscience 12(2):583-594.

Clarke, et al., "Reactive astrocytes express the embryonic intermediate neurofilament nestin," Neuroreport, 5 : 1885-1888, 1994.

Code, et al., "Some transforming growth factor-alpha connections and their colocalization with enkephalin in the rat central nervous system," Brain Res. 421:401-405, 1987.

Coffey, et al., "Production and auto-induction of transforming growth factor-α in human keratinocytes," Nature 328: 817-820, 1987.

Connor B., et al., "The Role of Neuronal Growth Factors in Neurodegenerative Disorders of the Hyman Brain," 1998 Brain Research Reviews 27: 1-39.

Cooper, et al, "Intrastriatal transforming growth factor α delivery to a model of parkinson's disease induces proliferation and migration of endogenous adult neural progenitor cells without differentiation into dopaminergic neurons", J. Neurosci. Oct. 13, 2004; 24(41):8924-8931.

From 1995 issue of SIGMA catalogue, Biochemicals Organic Compounds (Diagnostic Reagents) cover, copyright page and p. 1274.

Craig, et al., In Vivo Growth Factor Expansion of Endogenous Subependymal Neural Precursor Cell Populations in the Adult Mouse Brain , Journal of Neuroscience, New York, NY vol. 16, No. 8, Apr. 15, 1996, pp. 2649-2658, XP001002077, ISSN: 0270-6474.

Defeo-Jones, et al., "Structure-Function Analysis of Synthetic and Recombiant Derivatives of Transforming Growth Factor Alpha", Molecular & Cellular Biology (1988); 8(8):2999-3007.

Derynck, "Transforming Growth Factor-α " (1990) Molecular Reproduction and Development 27:3-9.

Dunbar, et al., "Structure-function and biological role of betacellulin," Intn'l J. of Biochem. & Cell Biol., 32(8):805-815, 2000.

Dhuria SV—J Pharm Sci 99:1654-1673—Intranasal delivery to the central nervous system: mechanisms and experimental considerations.—(2010).

Earp, et al., "Epidermal Growth Factor (EGF) Stimulates EGF Receptor Synthesis," J. Biol. Chem. 261 : 4777-4780, 1986.

Ebadi, et al, "Neurotrophins and Their Receptors in Nerve Injury and Repair" (1997) Neurochem. Int. 30(4/5):347-374.

Eriksson, et al., "Neurogenesis in the adult human hippocampus," NatMed 4:1313-1317—(1998).

Ezeonu, et al., "Cell fate decisions in a human retinal precursor cell line: basic fibroblast growth factor- and transforming growth factor-alpha-mediated differentiation", DNA Cell Bio.Sep. 2000; 19(9):527-37.

Ezeonu, et al., "Density-dependent differentiation in nontransformed human retinal progenitor cells in response to basic fibroblast growth factor-and transforming growth factor-alpha", DNA Cell Biol, Oct. 2003; 22(10): 607-20.

Faber-Elman et al, "Involvement of Wound-associated Factors in Rat Brain Astrocyte Migratory Response to Axonal Injury: In Vitro Simulation" (1996) J. Clin. Invest. 97(1):162-171.

Fallon, et al., "In vivo Induction of Massive Proliferation, directed Migration, and Differentiation of Neural Cells in the Adult Mammalian Brain", Proceedings of the National Academy of Sciences, USA, vol. 97:14686-14691 (2000).

Fallon, et al., "Functional Implications of the Anatomical Localization of Neurotrophic Factors", Neutrophic Factors, (Loughlin, S. E. & Fallon, J. H., Eds) 1993 Academic Press, New York, pp. 1-24.

Fallon, et al, "Localization of Cells Containing Transforming Growth Factor-α Precursor Immunoreactivity in the Basal Ganglia of the Adult Rat Brain", Growth Factors; 1990, 2:241-250.

Fallon, et al., "Epidermal Growth Factor Receptor mRNA Is Increased in the Striatum of Rats With 6ohba Lesions of the Substantia Kigra and Intrastriatal Transplants in the Caudate Putamen" Department of Anatomy and Neurobiology, University of California, Irvine, Irvine, CA 92717, Society for Neuroscience Abstracts vol. 20, 1994, p. 40.

Fallon, et al., "The Rat Nervous System", G. Paxinos, Ed., pp. 215-237, Academic Press, San Diego, 1995.

Fallon, et al., Cerebral Cortex, E.G. Jones and A. Peters, Eds., vol. 6, pp. 41-127, Plenum Press, New York, 1987.

Fallon, et al., "Epidermal Growth Factor Immunoreactive Material in the Central Nervous System: Location and Development," Science 224:1107-1109, (Jun. 8, 1984).

Fallon, "Growth Factors in the Basal Ganglia", The British Library—"The world's knowledge", (1986) pp. 247-260.

Fallon—Growth Factors 6:139-157—Localization of Acidic Fibroblast Growth Factor Within the Mouse Brain Using Biochemical and Immunocytochemical Techniques—(1992).

Fernaud-Espinoza, et al., "Differential Activation of Microglia and Astrocytes in Aniso- and Isomorphic Gliotic Tissue," Glia 8 : 277-291, 1993.

Ferrari, et al., "Epidermal Growth Factor Exerts Neuronotrophic Effects on Dopaminergic and GABAergic CNS Neurons: Comparison With Basic Fibroblast Growth Factor," J. Neurosci, Res. 30:493-497, 1991.

Ferri, et al., "Regulation of regional differences in the differentiation of cerebral cortical neurons by EGF family-matrix interactions," Development 121 : 1151-1160, 1995.

Fishman Renata et al, "Multiple Receptor Systems Promote CNS Neural Migration" Database Biosis Online, Biosciences Information Service, Philadelphia, PA, US; 1993, Database Accession No. PREV199396090915 XP002240919 & Journal of Neuroscience vol. 13, No. 8, 1993, pp. 3485-3495.

Freed, et al., "Eight Years Experience with Fetal Neurotransplantation in Patients with Advanced Parkinsons Disease," Soc. Neurosci. Abstr. 22 : 481-3, 1996.

Frey, II et al., "Delivery of 125I-NGF to the Brain via the Olfactory Route," Drug Delivery 4:87-92, 1997.

Friguls, et al., "Activation of ERK and Akt signaling in focal cerebral ischemia: modulation by.TGF-α and involvement of NMDA Receptor", Neurobiology of Disease 11, 443-456 (2002).

Fuxe, et al., "Trophic Regulation of the Basal Ganglia: Focus on Dopamine Neurons", Journal of Chemical Neuroanatomy 9 (1995) 79-80, Elsevier Science Ltd., Oxford UK, 1994, 618 pp., ISBN 0-08-042276-4.

Ghashghaei, et al., "Neuronal migration in the adult brain: are we there yet?", Nature Reviews Neuroscience, 8:141-151 (2007).
Gill, "Regulation of EGF Receptor Expression and Function" (1990) Molecular Reproduction and Development 27:46-53.
Gleason, et al., "Ependymal stem cells divide asymmetrically and transfer progeny into the subventricular zone when activated by injury", Neuroscience, vol. 156, Issue 1, Sep. 22, 2008, pp. 81-88.
Gomez-Pinilla, et al., "Epidermal growth factor receptor immunoreactivity in rat brain. Development and cellular locations," Brain Res. 438:385-390, 1988.
Gould E., et al., "Neurogenesis in the Neocortex of Adult Primates ," (Science 286:548-552—1999) p. 3, 13.
Greengard, et al., "Beyond the dopamine receptor: the DARPP-32/protein phosphatase-1 cascade," Neuron 23:435-447—(1999).
Grotendorst, et al., "EGF and TGF-alpha Are Potent Chemoattractants for Endothelial Cells and EGF-like Peptides are Present at Sites of Tissue Regeneration," J. Cell. Physiol.1989. 139:617-623.
Guerra-Crespo, et al., "Intranasal administration of PEGylated transforming growth factor-alpha improves behavioral deficts in a chronic stroke model." J. Stroke Cerebrovasc Dis. Jan. 2010:19(1):3-9.
Guerra-Crespo, et al., "Transforming Growth Factor-Alpha Induces Neurogenesis And Behavioral Improvement in a Chronic Stroke Model." Neuroscience, 160, 470-483 (2009).
Hadjiconstantinou, et al., "Epidermal Growth Factor Enhances Striatal Dopaminergic Parameters in the 1-Methyl-4-Phenyl-1,2,3,6-Tetrahydropyridine-Treated Mouse," J.Neurochem. 57:479-482, 1991.
Hefti F., "Neurotrophic Factor Therapy for Nervous System Degenerative Diseases," J.Neurobiol. 25:1418-1435, 1994.
Heidenkummer, et al., "Immunohistochemical localization of epidermal growth factor receptor in a human epiretinal membrane," (1991) Graefe's Arch Clin Exp Ophthalmol 229:492-496.
Hishiki, et al., "Glial Cell Line-derived Neurotrophic Factor/Neurturin-induced Differentiation and Its Enhancement by Retinoic Acid in Primary Human Neuroblastomas Express *c-Ret*, *GFRα-1*, and *GFRα-2*," Cancer Res. 58 : 2158-2165, (May 15, 1998).
Jackowski et al, "Neural injury repair: hope for the future as barriers to effective CNS regeneration become clearer", Br. J. of Neurosurg., 9:303-317, 1995.
Jin K., "Neurogenesis in dentate subgranular zone and rostral subventicular zone after focal cerebral ischemia in the rat," Proc Natl Acad Sci U S A 98:4710-4714—(2001).
Jonathan et al, "The Ortega Hypothesis", Science, vol. 178, pp. 368-375 (1972).
Ju, et al., "TGFα Enhances Locomotion of Cultured Human Keratinocytes," J. Invest Dermatol. 100 : 628-632, 1993.
Junier, et al., "Transforming Growth Factor a (TGFα) Expression in Degenerating Motoneurons of the Murine Mutant Wobbler: A Neuronal Signal for Astrogliosis?," J. Neurosci. 14 : 4206-4216, 1994.
Junier M-P., "What role(s) for TGFα in the central nervous system?," Prog. Neurobiol. 2000.62:443-473.
Kelly, et al., "Amphetamine and Apomorphine Responses in the Rat Following 6-OHDA Lesions of the Nucleus Accumbens Septi and Corpus Striatum," Brain Research, 94(3):507-522, Sep. 5, 1974.
Kesavan, et al., "Regulation of stability and synthesis of EGF-receptor MRNAs encoding for intact and truncated receptor forms," Oncogene 5 : 483-488, 1990.
Khalid Shah, "Neural Stem Cells and Armed Derivatives: Fate and Therapeutic Potential in the Brain", Gene Therapy and Regulation, 3(1):91-109, (2007).
Kireeva, et al., "Cyr61, a product of a growth factor-inducible immediate-early gene, promotes cell proliferation, migration, and adhesion," Mol. Cell. Biol., 16:1326, 1996.
Kirschenbaum, et al., "In vitro Neuronal Production and Differentiation by Precursor Cells Derived from the Adult Human Forebrain," Cerebral Cortex 4 : 576-589, 1994.
Knusel, et al., "Selective and Nonselective Stimulation of Central Cholinergic and Dopaminergic Development in vitro by Nerve Growth Factor, Basic Fibroblast Growth Factor, Epidermal Growth Factor, Insulin and the Insulin-like Growth Factors I and II," and nonJ. Neurosci. 10:558-570, 1990.

Kornblum, et al., "Prenatal Ontogeny of the Epidermal Growth Factor Receptor and Its Ligand, Transforming Growth Factor Alpha, in the Rat Brain," (1997) Jln. of Comparative Neurology 380:249-261.
Krushel, et al., "Neural cell adhesion molecule (N-CAM) inhibits astrocyte proliferation after injury to different regions of the adult rat brain," Proc. Natl. Acad. Sci . USA 92 : 4323-4327, 1995.
Kudlow, et al, "Inability of Anti-epidermal Growth Factor Receptor Monoclonal Antibody to Block "Autocrine" Growth Stimulation in Transforming Growth Factor-secreting Melanoma.Cells", J. Biol Chem 259(19):11895-900, 1984.
Kudlow, et al., "Transforming Growth Factor-a in the Mammalian Brain," J. Biol. Chem. 264:3880-3883, 1989.
Kuhn, et al., "Epidermal Growth Factor and Fibroblast Growth Factor-2 Have Different Effects on Neural Progenitors in the Adult Rat Brain." The Journal of Neuroscience, 17(15):5820-5829, Aug. 1, 1997.
Lachyankar, et al., "CNS Precursor Cells That Express TRK Receptors: Induction of Different Cell Fates by Neurothrophins," Soc. Neurosci. Abstr. 22 : 394.7, 1996.
Lazar, et al., "Regional Distribution and Developmental Expression of Epidermal Growth Factor and Transforming Growth Factor-α mRNA in Mouse Brain by a Quantitative Nuclease Protection Assay," J. Neurosci. 12:1688-1697, 1992.
Lee et al., "Developmental expression of rat transforming growth factor-alpha mRNA", Mol.Cell. Biol. 5:3655-3646, 1985.
Lee, et al., "Transforming growth factor alpha: expression, regulation, and biological activities," Pharmacol Rev 47:51-85—(1995).
Lefebvre, et al., "Regeneration of the neurosensory structures in the mammalian inner ear" (1997) Acta oto rhino-laryngologica belg. 51:1-10.
Leker, et al., "Transforming growth factor α induces angiogenesis and neurogenesis following stroke", Neuroscience 163 (2009) 233-243.
Lendahl, et al., "CNS Stem Cells Express a New Class of Intermediate Filament Protein," Cell 60 : 585-595, 1990.
Levine, et al., "Sonic Hedgehog Promotes Rod Photoreceptor Differentiation in Mammalian Retinal Cells In Vitro," J. Neurosci. : 6277-6288, 1997.
Lin, et al., "Expression of CD34 in endothelial cells, hematopoietic progenitors and nervous cells in fetal and adult mouse tissues," Eur. J. Immunol. 1995. 25:1508-1516.
Lindvall, et al., "Stem cells for the treatment of neurological disorders," Nature 441:1094-1096—(2006) p. 14.
Linnemann, et al.,"Expression of NCAM mRNA and Polypeptides in Aging Rat Brain," Int. J. Devel. Neurosci. 11 : 71-81, 1993.
Literature Search of Science Citations Index (Scisearch) database of Knight-Ridder Information Service, formerly the Dialog® Information Retrieval Service with complete list of citations and abstracts for articles citing Fallon et al. PNAS 97:14686-14691 (2000).
Literature Search Results from Science Citation Index (SciSearch) database for articles citing Kohler and Milstein article, *Nature* 256:495 (1975).
Lois, et al., "Proliferating subventricular zone cells in the adult mammalian forebrain can differentiate into neurons and glia," Proc. Natl. Acad. Sci. USA 90:2074-2077, 1993.
Lois, et al., "Chain Migration of Neuronal Precursors," Science 271 : 978-981, 1996.
Lokeshwar, et al., "Protamine Enhances Epidermal Growth Factor (EGF)-stimulated Mitogenesis by Increasing Cell Surface EGF Receptor Number," J. Biol. Chem. 264:19318-19326, 1989.
Loughlin, et al., "Mesostriatal Projections from Ventral Tegmentum and Dorsal Raphe: Cells Project Ipsilaterally or Contralaterally But Not Bilaterally", Neurosci. Lett. 32 : 11-16, 1982.
Loughlin et al., "6-OHDA lesion and TGF a infusion-induced plasticity in the nigrostriatal dopamine system—Tracing changes with markers for neurodegeneration", (1995) Soc. Neursci. Abs.
Loughlin, et al., "Efficacy of Intrastriatal Transplants: Role of Trophic Factors", The Basal Ganglia IV, (Percheron, G., et al., Eds) 1994, Plenum Press, New York, pp. 205-212.
Loughlin, et al., "Transforming Growth Factor Alpha: A Potential Role in the Efficacy of Intrastriatal Transplants", (1992) Soc. Neurosci. Abs.

Loughlin, et al.,"Striatal Transforming Growth Factor Alpha: Plasticity of Expression and Effects of Infusions of Dopaminergic Afferents", (1993) Soc. Neurosci. Abs.

Loughlin, et al., "Postnatal Ontogeny of Transforming Growth Factor, Alpha and Epidermal Growth Factor mRNA in Rat Brain", Dept. Anst. And Neurobio., Univ Calif., Irvine, Irvine, CA 92717, Society for Neuroscience Abstracts vol. 20, 1994, p. 40.

Louis, et al., "In vivo administration of EGF directly into the adult mouse subventricular zone has a greater effect on the frequency of neural progenitors than neural stem cells." Presented at Keystone 2005 by StemCell Technologies, Inc. www.stemcell.com.

Lundberg, et al., "Conditionally Immortalized Neural Progenitor Cells Grafted to the Striatum Exhibit Site-Specific Neuronal Differentiation and Establish Connections with the Host Globus Pallidus", Neurobiology of Disease, 3(1):33-50, Feb. 1996.

Luskin, M., "Restricted Proliferation and Migration of Postnatally Generated Neurons Derived from the Forebrain Subventricular Zone," Neuron 11 :173-189, 1993.

Ma, et al., "Intranasal delivery of transforming growth factor-beta1 in mice after stroke reduces infarct volume and increases neurogenesis in the subventricular zone," BMC Neurosci 9:117—(2008).

Martinez-Morales et al., "Vitronectin is expressed in the ventral region of the neural tube and promotes the differentiation of motor neurons," Development 124 : 5139-5147, (1997).

McInnes, et al., "Growth Factor Receptors: Structure, Mechanism, and Drug Discovery" (1998) Protein Engineering Network of Centres of Excellence, Univ. of Alberta, Canada.

Mezey, et al., "Turning Blood into Brain: Cells Bearing Neuronal Antigens Generated in Vivo from Bone Marrow," (2000) Science 290:1779.

Mogi, et al., "Interleukin-1B, interleukin-6, epidermal growth factor and transforming growth factor-$\alpha$ are elevated in the brain from parkinsonian patients," Neurosci. Lett. 180: 147-150, 1994.

Morrison, et al., "Trophic Stimulation of Cultured Neurons from Neonatal Rat Brain by Epidermal Growth Factor," Science 238:72-75, 1987.

Morshead, et al., "Postmitotic Death Is the Fate of Constitutively Proliferating Cells in the Subependymal Layer of the Adult Mouse Brain," J. Neurosci. 249-256, 1992.

Morshead, et al., "Neural Stem Cells in the Adult Mammalian Forebrain: A Relatively Quiescent Subpopulation of Subependymal Cells," Neuron 13 : 1071-1082, 1994.

Nakatomi, et al., "Regeneration of Hippocampal Pyramidal Neurons after Ischemic Brain zInjury by Recruitment of Endogeneous Neural Progenitors," Cell, 110:429-441 Aug. 23, 2002.

"New stroke therapy successful in rats: protein completely restores motor function", www.sciencedaily.com/releases/2010/01/100112135034.htm, Jan. 12, 2010.

NeuroRepair Validates IP with Lab's Success in New Stroke Therapy, www.nrweb.com/releases/neuroregenerative/theranv/nrweb3583304.htm , Jul. 28, 2010.

Nieto-Sampedro, et al., "Epidermal growth factor receptor immunoreactivity in rat brain astrocytes. Response to injury," Neurosci. Lett. 91 : 276-282, 1988.

Nihei, et al., "Newoflament and Neural Cell Adhesion Molecul.e Immunocytochemistry of.Huntington's Disease Striatum," Ann. Neurol. 31 : 59-63, 1992.

Otto, et al., "Basic FGF Reverses Chemical and Morphological Deficits in the Nigrostriatal System of MPTP-Treated Mice," J. Neuroscience, 10:1912-1921 (1990).

Pagani, et al., "Tissue-specific Splicing Pattern of Fibronectin Messenger RNA Precursor during Development and Aging in Rat," J. Cell Biol. 113 : 1223-1229, 1991.

Pan, et al., "TGF$\alpha$ and the Blood-Brain Barrier: Accumulation in Cerebral Vasculature", Exp. Neurol. 1999. 160:454-459.

Panagakos F., "Transforming Growth Factor—Alpha Stimulates Chemotaxis of Osteoblasts and Osteoblast-like Cells In Vitro," Biochem. Mol. Biol. Int. 33 : 643-650, 1994.

Pardridge WM, "Drug Targeting to the Brain," Pharm Res 24:1733:1744 (2007).

Park, et al., "Protection from 1-methyl-4-phenylpyridinium (MPP+) toxicity and stimulation of regrowth of MPP+-damaged dopaminergic fibers by treatment of mesencephalic cultures with EGF and basic FGF," Brain Res. 599:83-97, 1992.

Pawson et al. "Assembly of Cell Regulatory Systems Through Protein Interaction Domains", 2003, Science 300:445-452.

Pesheva, et al., "Expression and localization of the Fibronectin Receptor in the Mouse nervous System," J. Neurosci. Res. 20 : 420-430, 1988.

Pezzoli, et al., "Intraventricular Infusion of Epidermal Growth Factor Restores Dopaminergic Pathway in Hemiparkinsonian Rats", Movement Disorders (1991); 6(4):281-287.

Poltorak, et al., "Effects of Frontal Cortical Lesions on Mouse Striatum: Reorganization of Cell Recognition Molecule, Glial Fiber, and Synaptic Protein Expression in the Dorsomedial.Striatum," J. Neurosci. 13 : 2217-2229, 1993.

Popa-Wagner, et al., "Decortication and striatal mRNA: Increases of mRNA for fibronectin, but not of NCAM or $\alpha$-1 tubulin," Neuroreport 3 : 853-856, 1992.

Prieto, et al., "Localization during Development of Alternatively Spliced forms of Cytotactin mRNA by in Situ Hybridization," J. Cell Biol. 111: 685-698, 1990.

Quirion, et al., "Visualization of Growth Factor Receptor Sites In Rat Forebrain," Synapse 2:212-218, 1988.

Rahman M—Neurosurg Focus 27:E12—Early history of the sterotactic apparatus in neurosurgery—(2009).

Rakic P "Limits of Neurogenesis in Primates", Science 227:1054-1056 (1985).

Ray et al., "Characterization of Neural Progenitor Cells Isolated and Cultured From Different Regions of Adult Rat Spinal Cord," Soc. Neurosci. Abstr. 22 : 394-5 1996.

Raymond et al., "Characterization of Epidermal Growth Factor Receptor Induction by Retinoic Acid in a Chemically Transformed Rat Liver Cell Line", Cell. Growth Diff. 1 : 393-399, Sep. 1990.

Reid et al, "Radial Migration of Subependymal Cells in the Adult Rodent Forebrain", (1996).Soc. Neurosci. Abs.

Reid et al, Tyrosine Hydroxylase Immunoreactive Cells in Adult Rat Striatum After. Transforming Growth Factor Alpha Infusion & 6-Hydroxydopamine Lesion', Society for.Neuroscience Abstracts vol. 20, 1994, p. 40.

Reid et al, Abstracts,Society of Neuroscience Abstracts, vol. 22 Part 3, 26th Annual Meeting, Washington, D.C. Nov. 16-21, 1996.

Reid et al, Review of "Trophic regulation of the basal ganglia" J. Chemical Neuroanatomy, 1995; 9(2):79-80.

Reid et al., Radial Migration of Subependymal Cells in the Adult Rodent Forebrain, Abstract, Aug. 7, 1997, Dept. of Anatomy and Neurobiology, Uni. of CA, Irvine, CA.

Reid. Dissertation 1997.

Reneker et al., "TGFa can act as a chemoattractant to perioptic mesenchymal cells in developing mouse eyes," Development 121 : 1669-1680, 1995.

Report prepared by National Institutes of Health "Stem Cells: Scientific Progress and Future Research Directions", Chapter 8, Jun. 2001.

Reynolds, "Generation of Neurons and Astrocytes from Isolated Cells of the Adult Mammalian Central Nervous System," (1992) Science 255:1707-1710, 1992.

Reynolds et al., "A Multipotent EGF-Responsive Striatal Embryonic Progenitor Cell Produces Neurons and Astrocytes," J. Neurosci. 12 : 4565-4574, 1992.

Rimaniol, A.C. et al., "Cerebral trauma induces a biphasic cortical production of TGF$\beta$ flanking the transient elevation of TNF$\alpha$ and IL6" (1994) Abstract, J. NeuroImmunol. 54:1-2.

Robert Miller. "The promise of stem cells for neural repair" Brain Research 1091:258-264 (2006).

Rousselot, et al., "Embryonic (PSA) N-CAM reveals chains of migrationg neuroblasts between the lateral ventricle and the olfactory bulb of adult mice", The Journal of Comparative Neurology, 351(1):51-61, 1995.

Sagar et al, "Epidermal Growth Factor and Transforming Growth Factor $\alpha$ Induce c-fos Gene Expression in Retinal Muller Cells in Vivo" (1991) Jln. of Neuroscience Res. 29:549-559.

Sakane T, Pardridge WM, "Carboxyl-directed pegylation of brain-derived neurotrophic factor markedly reduces systemic clearance with minimal loss of biologic activity," Pharm Res 14:1085-1091 (1997).

Sanchez Ramos, "Adult Bone Marrow Stromal Cells Differentiate into Neural Cells in Vitro," (2000) Experimental Neurology 164:247.

Schmacher et al., "Intracerebral Implantation of Nerve Growth F Actor-Producing Fibroblasts Protects Striatum Against Neurotoxic Levels of Excitatory Amino Acids,"Neuroscience, abstract only, 45:561-570 (1991).

Schneider et al., "Enhanced restoration of striatel dopamine concentrations by combined OM! ganglioside and neurotrophic factor treatments," Brain Res. 674:260-264, 1995.

Seroogy et al., "Proliferative zones of postnatal rat brain express epidermal growth factor receptor mRNA," Brain Res. 670:157-164, 1995.

Seroogy et al., "Cellular Localization of Transforming Growth Factor-α mRNA in Rat Forebrain", J. Neurochem. 60 : 1777-1782, 1993.

Seroogy et al., "Expression of EGF receptor mRNA in rat nigrostriatal system", Neuroreport.6:105-108, 1994.

Skolnick et al, "From genes to protein structure and function: novel applications of computational approaches in the genomic era", Trends in Biotech, 18(1):34-39, 2000.

Snyder et al., "Neuronal Regeneration, Reorganization, and Repair," (1997) Adv. Neurol. 72:121-132.

Snyder et al., "Multipotent neural precursors can differentiate toward replacement of neurons undergoing targeted apoptotic degeneration in adult mouse neocortex," (1997) *Proc. Natl. Acad. Sci. USA* 94:11663-11668.

Svendsen et al., "Survival and Differentiation of Rat and Human Epidermal Growth Factor-Responsive Precursor Cells Following Grafting into the Lesioned Adult Central Nervous System", 1996, Experimental Neurology 137: 376-388.

Szele et al., "Cortical Lesions Induce an Increase in Cell Number and PSA-NCAM Expression in the Subventricular Zone of Adult Rats," J. Compo Neurol. 368: 439-454, 1996.

Szele et al., "Pattern of Expression of Highly PolYsialYla Ted Neural Cell Adhesion Molecule in the Developing and Adult Rat Stria Tum," Neurosci. 60 : 133-144, 1994.

'T Hart et al. "The use of animal models to investigate the pathogenesis of neuroinflammatory disorders of the central nervous system", Curr. Opin. Neurol. 2003. 16:375-383.

Tanabe et al., "Induction of motor neurons by Sonic hedgehog is independent of floor plate differentiation Yasuto Tanabe, Henk Roelink and Thomas M. Jessell," Curr. Biol. 5 : 651-658, 1995.

The recitation of "parenteral" in the 27th edition of Dorland's Illustrated Medical Dictionary.(1988) p. 1231.

Thompson et al., "Regulation of Epidermal Growth Factor Receptor Gene Expression by Retinoic Acid and Epidermal Growth Factor," J. Biol. Chem. 264 : 3230-3234, 1989.

Toma et al., "Spatiotemporal Increases in Epidermal Growth Factor Receptors following Peripheral Nerve Injury," J. Neurosci. 12 : 2504-2515, 1992.

Twardzik et al., "Vaccinia virus-infected cells release a novel polypeptide functionally related to transforming [transferring] and epidermal growth factors", Aug. 1985, Proc. Natl. Acad. Sci 82:5300-5304.

Venero et al., "Intrastriatal Infusion of Nerve Growth Factor After Quinolinic Acid Prevents Reduction of Cellular Expression of Choline Acetyl Transferase Messenger RNA and Trka Messenger Rna, But Not Glutamate Decarboxylase Messenger Rna," Neuroscience, abstract only, 61:257-268 (1994).

Ventrella et al, "Effect of intracerebroventricular infusion of epidermal growth factor in rats hemitransected in the nigro-striatal pathway", J. Neurosurg. (1993); 37:1-8.

Vicario-Abejon et al., "Cerebellar Precursors Transplanted to the Neonatal Dentate Gyrus Express Features Characteristic of Hippocampal Neurons," Neuron 15 : 105-114, 1995.

Vicario-Abejon et al., "Autoradiographic study of IZI llepidermal growth factor-binding sites in the mesencephalon of control and parkinsonian brains post-mortem," J. Neurosci. 15 : 6351-6363, 1995.

Villares et al., "Autoradiographic study of [12I I]epidermal growth factor-binding sites in the mesencephalon of control and parkinsonian brains post-mortem," Brain Res. 628: 72-76, 1993.

Weickert et al, Striatal TGF-α: postnatal developmental expression and evidence for a role in the proliferation of subependymal cells (1995) Developmental Brain Research 86:203-216.

Weiss et al, "Multipoint CNS Stem Cells Are Present in the Adult Mammalian Spinal Cord and Ventricular Neuroaxis", J. Neuroscience (1996); 16(23):7599-7609.

Werner et al., "Localization of Immunoreactive Epidermal Growth Factor Receptors in Human Nervous System," J. Histochem, Cytochem. 36:81-86, 1988.

Woodbury, "Adult Rat and Human Bone Marrow Stromal Cells Differentiate Into Neurons,".(2000) J. Neuroscience Research 61:364.

Wyss—Coray et al., "Increased Central Nervous System Production of Extracellular Matrix Components and Development of Hydrocephalus in Transgenic Mice Overexpressing Transforming Growth Factor-J31," Am. J. Pathol. 147 : 53-67, 1995.

Xian et al., "Roles of Transforming Growth Factor-a and Related Molecules in the Nervous.System," Mo. Neurobiol. 1999. 20:157-183.

Young et al., Neuronal Differentiation and Morphological Integration of Hippocampal Progenitor Cells Transplanted to the Retina of Immature and Mature Dystrophic Rats, (Mol. Cell. Neurosciences 16:197, 2000.

Zhang et al., "Transforming growth factor α and a PC12-derived growth factor induce neurites in PC12 cells and enhance the survival of embryonic brain neurons", Cell. Regul. 1:511-521, 1990.

Zhao C—Cell 132:645-660—Mechanisms and functional implications of adult neurogenesis—(2008).

Zurn e t al., "Combined Effects of GDNF, BDNF, and CNTF on Motoneuron Differentiation In Vitro," J. Neurosci. Res. 44 : 133-141, 1996.

*Neurorepair, Inc. v. The Nath Law Group* —Expert Report of Richard Warburg, Apr. 8, 2010.

*Neurorepair, Inc. v. The Nath Law Group* —Expert Report of James Fallon, Apr. 8, 2010.

*Neurorepair, Inc. v. The Nath Law Group* —Expert Report of Marc J. Tetel, Apr. 8, 2010.

*Neurorepair, Inc. v. The Nath Law Group* —Rebuttal Expert Report of James Fallon, Apr. 22, 2010.

*Neurorepair, Inc. v. The Nath Law Group* —Supplemental Expert Report of Marc J. Tetel, Oct. 25, 2010.

*Neurorepair, Inc. v. The Nath Law Group* —Rebuttal Expert Report of Richard Warburg, Apr. 23, 2010.

*Neurorepair, Inc. v. The Nath Law Group* —Supplemental to Rebuttal Expert Report of Richard Warburg, Oct. 13, 2010.

*Neurorepair, Inc. v. The Nath Law Group* —Second Rebuttal Expert Report of Richard Warburg, Nov. 12, 2010.

*Neurorepair, Inc. v. The Nath Law Group* —Second Supplemental to Rebuttal Expert Report of Richard Warburg, Mar. 24, 2011.

* cited by examiner

METHODS FOR TREATING NEUROLOGICAL DEFICITS

This application is a continuation of U.S. patent application Ser. No. 09/129,028, filed Aug. 4, 1998 (now U.S. Pat. No. 7,790,669), which claims benefit and priority from U.S. Provisional Patent Application 60/055,383, filed Aug. 4, 1997. All the prior applications are incorporated herein by reference in their entirety.

The field of the invention is treatment of neurological deficits caused by an injury, disease, or developmental disorder that affects the central nervous system.

BACKGROUND OF THE INVENTION

Neurotrophic factors are peptides that variously support the survival, proliferation, differentiation, size, and function of nerve cells (for review, see Loughlin and Fallon, *Neurotrophic Factors*, Academic Press, San Diego, Calif., 1993). While the numbers of identified trophic factors, or growth factors, are ever-increasing, most can be assigned to one or another established family based upon their structure or binding affinities. Growth factors from various families, including the epidermal growth factor (EGF) family, have been demonstrated to support dopaminergic neurons of the nigrostriatal system (an area that can be treated according to the methods of the present invention) (for review, see Hefti, *J. Neurobiol.* 25:1418-1435, 1994; Unsicker, *Prog. Growth Factor Res.* 5:73-87, 1994).

EGF, the founding member of the EGF family, was characterized more than 25 years ago (Savage and Cohen, *J. Biol. Chem.* 247:7609-7611, 1972; Savage et al., *J. Biol. Chem.* 247:7612-7621, 1972). Since then, additional members have been identified; they include vaccinia virus growth factor (VGF; Ventatesan et al., *J. Virol.* 44:637-646, 1982), myxomavirus growth factor (MGF; Upton et al., *J. Virol.* 61:1271-1275, 1987), Shope fibroma virus growth factor (SFGF; Chang et al., *Mol. Cell. Biol.* 7:535-540, 1987), amphiregulin (AR; Kimura et al., *Nature* 348:257-260, 1990), and heparin-binding EGF-like growth factor (HB-EGF; Higashiyama et al., *Science* 251:936-939, 1991). A common feature of these factors is an amino acid sequence containing six cysteines that form three disulfide cross links and support a conserved structure that underlies their common ability to bind the EGF receptor.

EGF is by far the most-studied member of the family and was the first localized to brain tissue: EGF-like immunoreactivity (IR) was found in areas of developing adult forebrain and midbrain including the globus pallidus, ventral pallidum, entopeduncular nucleus, substantia nigra, and the Islands of Calleja (Fallon et al., *Science* 224:1107-1109, 1984).

Another member of the EGF family, TGFα, has also been localized to brain tissue. It binds the EGF receptor (Todaro et al., *Proc. Natl. Acad. Sci. USA* 77:5258-5262, 1980), stimulates the receptor's tyrosine kinase activity, and elicits similar mitogenic responses in a wide variety of cell types (for review, see Derynck, *Adv. Cancer Res.* 58:27-52, 1992). TGFα might also bind to additional, unidentified receptors (which may help explain its differential actions in some cells). TGFα-IR has previously been shown to be heterogeneously distributed in neuronal perikarya throughout the adult rat CNS and in a subpopulation of forebrain astrocytes (Code et al., *Brain Res.* 421:401-405, 1987; Fallon et al., *Growth Factors* 2:241-250, 1990). TGFα mRNA has been detected in whole rodent brain (Lee et al., *Mol. Cell. Biol.* 5:3655-3646, 1985; Kudlow et al., *J. Biol. Chem.* 264:3880-3883, 1989) and in striatum and other brain regions by a nuclease protection assay (Weickert and Blum, *Devel. Brain Res.* 86:203-216, 1995) and by in situ nucleic acid hybridization (Seroogy et al., *Neuroreport* 6:105-108, 1994).

TGFα and EGF mRNAs reach their highest relative abundance (compared to total RNA) in the early postnatal period and decrease thereafter, suggesting a role in development (Lee et al., 1985, supra; Lazar and Blum, *J. Neurosci.* 12:1688-1697, 1992). In whole brain, the reduction is over 50% (Lazar and Blum, 1992, supra), whereas, in striatum, relative TGFα mRNA drops by two-thirds from peak levels (Weickert and Blum, 1995, supra). At all developmental stages examined, whole brain TGFα mRNA exceeds EGF mRNA levels by more than an order of magnitude (Lazar and Blum, 1992, supra).

The EGF receptor was localized by immunocytochemistry to astrocytes and subpopulations of cortical and cerebellar neurons in rat brain and to neurons in human autopsy brain specimens (Gomez-Pinilla et al., *Brain Res.* 438:385-390, 1988; Werner et al., *J. Histochem. Cytochem.* 36:81-86, 1988). EGF binding sites were revealed in rat cortical and subcortical areas, including the striatum, in an autoradiography study with radiolabeled EGF (Quirion et al., *Synapse* 2:212-218, 1988). In situ hybridization studies demonstrated EGF receptor mRNA in striatum and cells of the ventral mesencephalon (Seroogy et al., 1994, supra) and in proliferative regions in developing and adult rat brain (Seroogy et al., *Brain Res.* 670:157-164, 1995). As with relative EGF and TGFα mRNAs, EGF receptor mRNA is most abundant in striatum and ventral midbrain early in development, and gradually declines as the animal matures (Seroogy et al., 1994, supra).

Physiologically, TGFα acts on numerous cell types throughout the body, including many of neural origin (for review, see Derynck, 1992, supra). It supports the survival of cultured central neurons (Morrison et al., *Science* 238:72-75, 1987; Zhang et al., *Cell. Regul.* 1:511-521, 1990) and, unlike EGF, enhances survival and neurite outgrowth of dorsal root ganglion sensory neurons (Chalazonitis et al., *J. Neurosci.* 12:583-594, 1992). It also stimulates proliferation and differentiation of neuronal and glial progenitor cells from developing and adult brains (Anchan et al., *Neuron* 6:923-936, 1991).

The trophic effects of EGF-family peptides on mesencephalic dopaminergic neurons in culture have also been studied in recent years. EGF enhances the survival of E16 dopamine neurons in mixed midbrain cultures (Casper et al., *J. Neurosci. Res.* 30:372-381, 1991), but the degree to which it stimulates dopamine uptake is modest (Knusel et al., *J. Neurosci.* 10:558-570, 1990). TGFα also supports the survival of mesencephalic dopamine neurons in dissociated cell culture, but its effect is more selective than that of EGF (Ferrari et al., *J. Neurosci. Res.* 30:493-497, 1991; Alexi and Hefti, *Neurosci.* 55:903-918, 1993).

Another important characteristic of EGF-family growth factors is their ability to protect midbrain dopamine cells from neurotoxic assaults. EGF has been shown to protect dopamine neurons from glutamate or quisqualate excitotoxicity in dissociated cell culture (Casper and Blum, *J. Neurochem.* 65:1016-1026, 1995). It has also been demonstrated to protect cultured dopamine cells from the selective dopamine neurotoxin, 1-methyl-4-phenylpyridinium (MPP$^+$; Park et al., *Brain Res.* 599:83-97, 1992) and to increase dopamine uptake in MPP$^+$-treated cultures (Hadjiconstantinou et al., *J. Neurochem.* 57:479-482, 1991).

The results of studies with EGF in vivo were consistent those obtained in culture; EGF effected neuroprotection in both instances. For example, intracerebroventricular (ICV) infusions of EGF reduced amphetamine-induced rotations, increased the number of surviving tyrosine hydroxylase immunoreactive (TH-IR) cells in the SN, and increased striatal TH-IR fibers after transection of the nigrostriatal pathway in a rat model of PD (Pezzoli et al., *Movement Disord.* 6:281-287, 1993; Ventrella, *J. Neurosurg. Sci.* 37:1-8, 1993). ICV infusions of EGF into the brains of 1-methyl-4-phenyl-1,2,3,6-tetrahydropyridine (MPTP) lesioned mice enhanced the content of dopamine and 3,4-dihydro-zyphenylacetic acid (DOPAC) and the activity of tyrosine hydroxylase in the striatum (Hadjiconstantinou et al., 1991, supra; Schneider et al., *Brain Res.* 674:260-264, 1995).

Despite its more potent activity in vitro, relative to EGF, the trophic effects of TGFα in vivo—particularly in animals, including humans, with neurological deficits—are undetermined. The present invention is based on newly discovered effects of TGFα infusion on cells in the normal and abnormal (lesioned) central nervous system, which are described herein.

SUMMARY OF THE INVENTION

The present invention features methods and compositions for treating a patient who has a neurological deficit. The method can be carried out, for example, by contacting (in vivo or in culture) a neural progenitor cell of the patient's central nervous system (CNS) with a polypeptide that binds the epidermal growth factor (EGF) receptor and directing progeny of the proliferating progenitor cells to migrate en masse to a region of the CNS in which they will reside and function in a manner sufficient to reduce the neurological deficit. The method may include a further step in which the progeny of the neural precursor cells are contacted with a compound that stimulates differentiation.

Other objects, advantages, and novel features of the present invention will become apparent from the brief description of the drawings, the detailed description of the invention, and the working examples that follow.

BRIEF DESCRIPTION OF THE DRAWINGS

In FIG. 2A a "sense" probe was applied as a control. In FIGS. 2B-2D, sections through the substantia nigra (sn) reveal moderately abundant expression in the hippocampus (hip), the medial portion of the sna, and the parabranchial and paranigral nuclei of the ventral tegmental area (vta). In the most-caudal midbrain (FIG. 2D), the interpeduncular nucleus (ip) was the most intensely labeled. Scale bar=5 mm.

In FIG. 8A, silver staining in the caudate-putamen ipsilateral to the treatments reveals huge numbers of cells in the dorsal portion of the ridge, many of which exhibit an elongated morphology and are oriented normal to the subependymal region. There is also an increase in the number of cells along the lateral ventricle (lv). In the contralateral striatum (FIG. 8B), the cellular population is not expanded, either in the striatum or along the lateral ventricle.

In FIG. 9A, after four days of infusion, cellular expansion in the subependymal region is barely detectable above background staining. In FIG. 9B, after six days of infusion, the aggregation of thionin-stained cells near the lateral ventricle is much more robust. In FIG. 9C, after nine days of infusion, a region of densely-stained cells appears slightly lateral to the subependymal zone at the ventral end of the cellular expansion. In FIG. 9D, after fourteen days of infusion, a dense, well-formed ridge is evident well into the body of the striatum.

In FIG. 10A, nestin immunohistochemistry reveals an intense striatal ridge. In FIG. 10B, thionin staining of a near-adjacent section confirms the registry between the nestin-IR cells and the striatal ridge.

11A, where the infusion cannula was implanted in the far-lateral striatum, the ridge parallels the subependymal zone and is less dense than that seen with a mid-striatal infusion. In FIG. 11B, where the infusion cannula was implanted mid-striatum, the ridge is characteristically S-shaped, with the ventral portion extending far out into the ventral striatum. In FIG. 11C, where the infusion was immediately adjacent to the lateral ventricle, the striatal ridge is L-shaped and generally exhibits very dense thionin staining.

DETAILED DESCRIPTION

I. The Striatum and Nigrostriatal System

A. Anatomy, Connectivity and Neurochemistry

Figure 1:
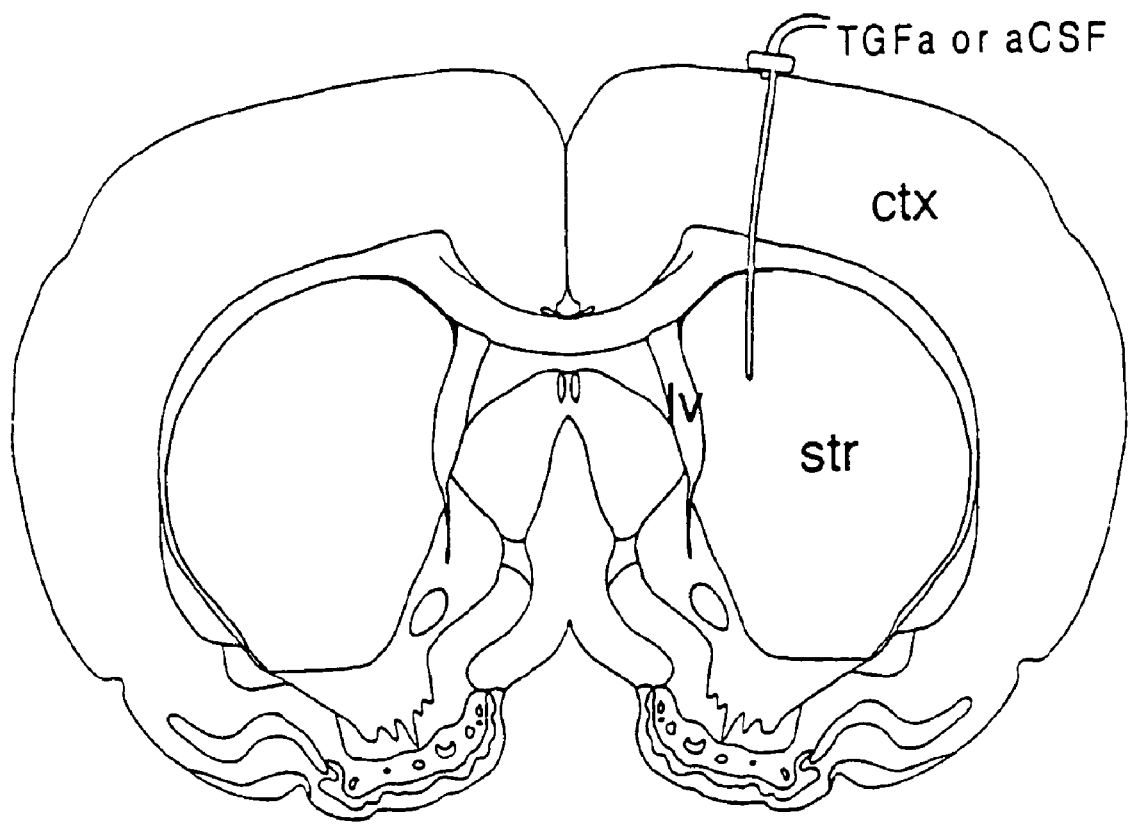
FIG. 1 is a schematic of a coronal section of rat forebrain. The injection pipette illustrated on the right-hand side represents one location into which a growth factor can be infused, the striatum (str). (cerebral cortex=ctx; lateral ventricle=lv).

Within the brain, the striatum, pallidum, substantia nigra, ventral tegmental area (VTA), subthalamic nucleus, and amygdala are collectively referred to as the basal ganglia. The striatum contains dorsal and ventral components, each of which is further subdivided into additional anatomical structures. In humans, the dorsal striatum consists of the caudate nucleus and the putamen. The C-shaped caudate follows the curve of the lateral ventricles. Its tail portions extend past the ends of the inferior horns and joins the amygdala in each temporal lobe. The head of the caudate turns ventrally from the anterior end of the anterior horns and fuses with the putamen. Although largely anatomically distinct in the human brain, they are combined into a common structure, the caudate-putamen or caudoputamen, in rodents.

The ventral striatum is comprised of the nucleus accumbens, olfactory tubercle, and the associated striatal cell bridges. The pallidum includes the globus pallidus, entopeduncular nucleus, substantia nigra pars reticulata (SNr), and the ventral pallidum. The entopeduncular nucleus and SNr have very similar afferent and efferent connections. The ventral pallidum contains regions that have a mix of connections that are similar to both the globus pallidus and entopeduncular nucleus. The other part of the substantia nigra, the pars compacta (SNc), includes dopamine neurons that span the substantia nigra-ventral tegmental area (SN-VTA), as well as dopamine cell clusters in the SNr. The circuitry of the basal ganglia is complex, but is very similar in both rats and humans (Fallon and Loughlin, *Cerebral Cortex*, E. G. Jones and A. Peters, Eds., Vol. 6, pp. 41-127, Plenum Press, New York, 1987; Alheid and Heimer, *Progr. Brain Res.* 107:461-484, 1996), making the rat a useful model for studying connections, neurochemistry, pharmacology, function, and clinical correlates of this system in the mammalian brain.

The striatum, together with other nuclei of the basal ganglia, contributes to the regulation of movement and emotion. A number of diseases affecting the system or its innervation are associated with profoundly debilitating motor impairment, often accompanied by affective disorders.

The caudate and putamen are the primary input nuclei of the basal ganglia and receive major excitatory projections from the cerebral cortex and the centromedian and intralaminar nuclei of the thalamus. Corticostriatal afferents are glutamatergic. Afferents from the thalamus are also thought to be glutamatergic. The substantia nigra pars compacta (SNc) provides dense dopaminergic input to the striatum via the nigrostriatal pathway (for review of this system in the rat, see Fallon and Loughlin, *The Rat Nervous System*, G. Paxinos, Ed., pp. 215-237, Academic Press, San Diego, 1995). The ventral striatum and nucleus accumbens receive the bulk of their dopaminergic innervation from dopamine cells of the VTA in the ventromedial mesencephalon. Limbic afferents from the amygdala and serotonergic fibers from the midbrain or raphe also terminate in the ventral striatum.

The distribution of striatal afferents and their terminations are not simply uniform representations of their regions of origin. The striatum is organized into patches or striosomes embedded in a functionally and chemically distinct surrounding matrix. This organization was originally demonstrated using histochemistry for acetylcholinesterase (AChE), which selectively stains the matrix (Graybiel and Ragsdale, *Proc. Natl. Acad. Sci. USA*, 75:5723-5726, 1978). Since then, enzyme histochemistry, immunocytochemistry, in situ hybridization, receptor binding with radiolabeled ligands, anterograde degeneration and other methods have been used to identify many additional markers that are differentially distributed in the two compartments. Markers for the matrix include calbindin, somatostatin, and dopamine uptake ($[^3H]$ mazindol binding) sites (Gerfen, *J. Comp. Neurol.* 236:454-476, 1985; Voorn et al., *J. Comp. Neurol.* 289:189-201, 1989). Striosomes can be identified by their higher relative abundance of enkephalin, 5'-nucleotidase activity with nigrostriatal lesions, tyrosine hydroxylase, mu opioid receptor binding, and substance P (Graybiel et al., *Neurosci.* 6:377-397, 1981; Schoen and Graybiel, *J. Comp. Neurol.* 322:566-576, 1992). As might be expected, however, there are interspecific and developmental variations in many of these markers and some are useful only in certain regions of the striatum.

The heterogeneity of chemical markers is further complicated by the selective origin and termination of many striatal pathways in the patch or matrix compartments. For instance, afferents from motor, cingulate, somatosensory and visual areas of cortex terminate in the matrix (Gerfen, *Nature* 311: 461-464, 1984; Donoghue and Herkenham, *Brain Res.* 365: 397-403, 1986). The bulk of the corticostriatal afferents from deep layer V and layer VI of limbic cortex terminate in the patches while most from more superficial layer V and layers II and III provide input to the matrix (Gerfen, *Science* 246: 385-388, 1989). Afferents from the VTA and the dorsal tier of the SNc provide dopaminergic input to the matrix. The patches receive dopamine innervation from the ventral tier of the SNc and dopamine cell clusters in the SNr (Schoen and Graybiel, *J. Comp. Neurol.* 322:566-576, 1992). In the dorsal striatum, inputs from nuclei in the medial division of the thalamus terminate in the patches while afferents from the lateral division—including anterior and posterior intralaminar and rostral ventral tier nuclei—predominantly innervate matrix tissue (Ragsdale and Graybiel, *J. Comp. Neurol.* 311: 134-167, 1991). In addition, amygdalostriatal fibers originating in the basolateral nucleus of the amygdala selectively innervate the patch compartment (Ragsdale and Graybiel, *J. Comp. Neurol.* 269:506-522, 1988).

Striatal efferents are also differentially distributed with respect to the patch-matrix organization. The striatonigral pathway, one of the two major pathways originating in the striatum, has been shown to be comprised of two distinct projections. Fibers arising from neurons in the patch compartment terminate around dopamine neurons in the ventral SNc and in dopamine cell clusters in the SNr. Matrix neurons give rise to topographically-arranged projections to the SNr, including non-dopaminergic areas and dopamine neurons whose dendrites are located in the SNr (Gerfen, 1984, supra; Jiminez-Castallanos and Graybiel, *Neurosci.* 32:297-321, 1989).

The other major efferent projection, the striatopallidal pathway, projects to the globus pallidus. It has not been shown to be distributed with respect to the patch-matrix organization; however, it is neurochemically distinct from the striatonigral system. The majority of striatopallidal fibers express enkephalin and not dynorphin or substance P. In contrast, few striatonigral projections contain enkephalin, but most express dynorphin and substance P (Gerfen and Young, *Brain Res.* 460:161-167, 1988). In primates, the two systems also differ in their anatomical regions of origin: striatopallidal efferents arise mainly from the putamen while striatonigral efferents originate primarily in the caudate (Parent et al., *Brain Res.* 303:385-390, 1984).

In addition to the heterogeneous distribution of striatal connections, several morphologically and chemically distinct types of neurons are found in the striatum (Albin et al., *Trends Neurosci.* 12:366-375, 1989; Groves, *Brain Res. Rev.* 5:234-238, 1983). They are traditionally classified as either spiny or aspiny based on their dendritic morphology. There are two generally recognized types of spiny neurons in the striatum. They contain various combinations of GABA, substance P, enkephalin and dynorphin, but are predominantly GABAergic. The medium spiny neurons (spiny type I) are by far the most abundant, comprising 90-95% of all striatal neurons. They have smooth cell bodies and dense accumulations of spines on the distant portions of their dendrites. Their dendritic arborizations range to about 200 μm from the somata. Medium spiny neurons are the principle terminal targets for dopaminergic neurons in the SNc, which form synapses predominantly on the necks of the dendritic spines. Spiny type II neurons are much larger, with variable arbors extending up to about 600 μm from the soma.

Spiny neurons are the projection neurons of the striatum. Those in the matrix containing GABA and substance P project predominantly to the internal segment of the globus pallidus ($GP_i$) and the SNr. Spiny GABAergic matrix neurons containing enkephalin, on the other hand, innervate the external segment of the globus pallidus ($GP_e$). Spiny neurons in the patch compartment send the majority of their efferents to the SNc (Albin et al., 1989, supra).

Striatal projection neurons of the two major efferent pathways can also be distinguished by their dopamine receptor subtypes. Substance P/dynorphin neurons projecting to the substantia nigra express predominantly $D_1$ dopamine receptors, while enkephalinergic striatopallidal neurons express mainly $D_2$ receptors. Neither receptor type, however, is expressed exclusively in either projection (Besson et al., *Neurosci.* 26:101-119, 1989; Gerfen et al., *Science* 250:1429-1432, 1990).

Three recognized types of aspiny neurons make up the population of striatal interneurons (Groves, 1983, supra; Carpenter, In: *Core Text of Neurosciences*, pp. 325-360, Williams and Wilkins, Baltimore, 1991). Together, they make up 10% or less of the total number of neurons of the striatum. Aspiny type I neurons are the most common of the three and have smooth dendrites in arbors slightly smaller than those of medium spiny neurons. They are largely GABAergic, but many contain somatostatin and neuropeptide Y. Aspiny type II neurons are distinguished by their large cell bodies and AChE and choline acetyltransferase (ChAT) staining. This cell type forms symmetric synapses with medium spiny neurons. Medium aspiny type III neurons are the least well characterized but are thought to contain GABA. There are probably additional chemically-defined and connectionally-defined subsets of these classes of neurons beyond the ones already identified.

B. Topography and Development

Experiments with anterograde and retrograde tracers in striatal projections of the mesencephalic dopamine system revealed precise topographies in adult rodents (Fallon and Moore, *J. Comp. Neurol.* 180:545-580, 1978). The dorsal striatum receives dopaminergic innervation from neurons in the ventral and intermediate SN and VTA. The ventral striatum and nucleus accumbens receive dopaminergic input from the dorsal VTA and intermediate SN (Fallon, *Ann. NY Acad. Sci.* 537:1-9, 1988).

Neurogenetic gradients in the developing system parallel the topographic arrangements of projections in the mature system. The dorsolateral portion of the SN is the earliest produced in the embryo, before embryonic day 15 (E15) in the rat (Altman and Bayer, *J. Comp. Neurol.* 198:677-716, 1981). Projections from this region innervate the lateral and ventral regions of the striatum (Carter and Fibiger, *Neurosci.* 2:569-576, 1977; Veening et al., *Neurosci.* 5:1253-1268, 1980), which are also the earliest striatal areas generated (Bayer, *Neurosci.* 4:251-271, 1984). As the striatum is populated with younger neurons in a ventrolateral-to-dorsomedial gradient, afferents arrive from more ventromedial (and later-produced) portions of the SN (generated after E15) to innervate these later-produced striatal areas. Thus, the youngest (ventromedial) nigral dopamine neurons innervate the youngest (dorsomedial) striatal neurons, and older (dorsolateral) nigral dopamine neurons innervate older (ventrolateral) striatal neurons. This pattern is repeated in the GABAergic striatonigral projections as well (Bunney and Aghajanian, *Brain Res.* 117:423-435, 1976).

The neurons of the striatum are derived from a neuroepithelium surrounding the lateral ventricles in the prenatal and early postnatal brain. A ventricular zone initially lines the ventricles, later joined by the subventricular (or subependymal) zone just deep to it. As the brain matures, the ventricular zone disappears, but the subependymal zone persists as a thin layer of cells. This zone contains neural stem cells and progenitor cells that migrate along a defined and restricted path to replenish the labile interneuronal cell population of the olfactory bulb (Luskin, *Neuron* 11:173-189, 1993; Lois and Alvarez-Buylla, *Science* 264:1145-1148, 1994).

C. Pathology

The striatum and its dopaminergic innervation are vulnerable to a number of conditions including several neurodegenerative diseases (Albin et al., 1989, supra) such as Huntington's disease (HD) and Parkinson's disease (PD). HD is an autosomal dominant hereditary disease (chromosome 4) characterized by progressive degeneration of the striatum. It is associated with involuntary choreathetotic movements of the limbs and face and disruptions of voluntary movement (for review, see Purdon et al., *J. Psychiatr. Neurosci.* 16:359-367, 1994). Medium spiny GABAergic neurons in the matrix compartment are most affected, especially the GABA/enkephalinergic neurons projecting to the $GP_e$ (Albin et al., 1989, supra). Large aspiny cholinergic interneurons and small aspiny interneurons containing somatostatin, neuropeptide Y and NADPH-diaphorase, also found in the matrix compartment, are relatively spared (Ferrante et al., *Science* 230:561-563, 1985; Reiner et al., *Proc. Natl. Acad. Sci. USA* 85:5733-5737, 1988). In more advanced stages of HD, however, neuronal degeneration includes all types of striatal neurons and extends to other nuclei of the basal ganglia, the cerebral cortex, hypothalamus, and cerebellum.

Parkinson's Disease (PD) is characterized by resting tremor, rigidity, inability to initiate movement (akinesia) and slowness of movement (bradykinesia) (Marsden, *Lancet* 335: 948-952, 1990). The motor deficits are associated with progressive degeneration of the dopaminergic nigrostriatal pathway and, to various extents, loss of dopaminergic innervation to the nucleus accumbens and degeneration of noradrenergic cells of the locus ceruleus and serotonergic neurons of the raphe (Javoy-Agid et al., *Adv. Neurol.* 40:189-198, 1984; Agid, *Lancet* 337:1321-1327, 1991). Up to 80% of nigral dopamine neurons can be lost before significant motor deficits are manifest.

One of the major strategies for using peptides known as neurotrophic factors as therapeutic agents in the treatment of neurodegenerative diseases is to arrest the degenerative process and enhance the function of remaining cells. The studies presented in the Examples below will illustrate how the present invention expands the use of neurotrophic factors beyond that which has been previously suggested.

II. Treatment of Neurological Deficits

As demonstrated by the examples below, neural precursors in the adult forebrain subependymal zone can be stimulated to proliferate and migrate en masse into the central nervous system (CNS) (e.g., into the striatum) in response to an infusion of a polypeptide that binds the EGF receptor (e.g., TGFα; the term "polypeptide" as used herein refers to any chain of amino acid residues, regardless of length or post-translational modification). Furthermore, one can direct migration of the proliferating cells as a dense ridge. As described below, directed migration can be accomplished in a variety of ways. For example, it is facilitated by denervation of the target region (which can be achieved by neurochemical or mechanical forces), by application of a polypeptide growth factor (e.g., TGFβ, which increases the regional expression of cell adhesion molecules such as fibronectin and laminin), and by contacting the cells along a desired migratory path with a compound that inhibits a naturally occurring signal that would otherwise inhibit migration (i.e., creating a permissive microenvironment by inhibiting an inhibitor).

Moreover, the shape of the migratory ridge can be controlled by varying the location of the infusion (e.g., by altering the placement of the infusion cannula or of a biodegradable capsule containing the active compound(s) of the invention). Similarly, the number of cells within the ridge can be controlled by varying the dosage of the active compound(s) (e.g., the dosage of TGFα) or the distance at which it is released relative to the population of neural precursor cells in the subependymal region. As described below (and as illustrated in FIGS. 10A, 10B, 11A, 11B, and 11C), when animals received mid-striatal or medial striatal infusions, the migrating cells stopped before they reached the infusion cannulae, which resulted in S-shaped or L-shaped ridges. Thus, it is possible not only to facilitate the cells' migration, but to control where that migration ends. Adjusting the dose and the location of release of the growth factor (and perhaps other compounds) may allow restriction of the area affected to a relatively limited target region.

The proliferation and migration of neural precursor cells in the adult mammalian brain are distinct events that can be controlled separately. Intracerebroventricular (ICV) or intrastriatal infusions of TGFα or EGF without deafferentation can induce proliferation, but degenerating, damaged (e.g., by deafferentation or other injury), or otherwise abnormal (i.e., malfunctioning) cells must be present to facilitate migration, at least on a scale that is large enough to impact recovery from an associated neurological deficit. As described further below, one can mimic the facilitating effect of degenerating, damaged, or otherwise abnormal cells with pharmacological agents. For instance, one can stimulate transient expression of cell adhesion molecules in the striatum by administering an inductive compound. For example, fibronectin is strongly upregulated by transforming growth factor beta (TGFβ) in cultures of cerebellar astrocytes (Baghdassarian et al., *Glia* 7:193-202, 1993). In transgenic mice overexpressing TGFβ, fibronectin and laminin are also strongly increased in the CNS over normal levels (Wyss-Coray et al., *Am. J. Pathol.* 147:53-67, 1995). Thus, directing migration with any compound that stimulates the expression of extracellular matrix molecules or cell adhesion molecules, particularly along the desired path of migration, is considered within the scope of the present invention.

Forebrain neural stem cells, which give rise to the migrating progenitors, are believed to remain in place along the ventricular wall (Morshead et al., *Neuron* 13:1071-1082, 1994). In the experiments described below, a region of intense EGF receptor hybridization persisted along the lateral ventricle after the migratory ridge had moved into the striatum. In addition, elongated cells were always found between the ridge and the lateral ventricle. Thus, despite the mass cellular migration away from the subependymal zone, the stem cells themselves likely were not part of the migrating ridge. These neural stem cells would provide a renewable source of new neurons and glia. Therefore, multiple waves of neural progenitor cells can be stimulated to migrate into regions of the brain that are injured, or that have degenerated or that otherwise contribute to a neurological deficit. The persistence of these cells also suggests that the normal function of stem cells in the adult forebrain—presently thought to provide new neurons for the olfactory bulbs—should not be irreversibly disrupted by the treatments.

Abundant striatal expression of TGFα (and its mRNA) and a lack of dopaminergic innervation also characterize the early developing striatum (Weickert and Blum, *Devel. Brain Res.* 86:203-216, 1995; Bayer, *Intl. J. Devel. Neurosci.* 2:163-175, 1984). Similarly, the increased EGF receptor mRNA expression in the subependymal region in TGFα-infused animals mimics the abundant EGF receptor mRNA hybridization observed in the periventricular neuroepithelium in the developing brain (Seroogy et al., *Neuroreport* 6:105-108, 1994; Seroogy et al., *Brain Res.* 670:157-164, 1995). Messenger RNAs encoding forms of fibronectin, and its receptor, and other cell adhesion molecules, which may facilitate the migration of neural precursors, are also developmentally regulated (Pesheva et al., *J. Neurosci. Res.* 20:420-430, 1988; Prieto et al., *J. Cell Biol.* 111:685-698, 1990; Pagani et al., *J. Cell Biol.* 113:1223-1229, 1991; Linnemann et al., *Int. J. Devel. Neurosci.* 11:71-81, 1993). Thus, one way to conceptualize the effects observed in the TGFα-infused and 6-OHDA lesioned animals in the present studies is as a selective recapitulation of embryonic neurogenesis. That is, neural stem cells in the adult mammalian brain may respond to proliferation signals and their progeny may respond to migration signals as they do in the developing animal.

Neural stem cells have recently been found in subependyma throughout the adult rodent CNS (Weiss, *Soc. Neurosci. Abstr.* 25:101, 1995; Ray et al., *Soc. Neurosci. Abstr.* 22:394.5, 1996) and in the subependyma of the adult human forebrain (Kirschenbaum et al., *Cerebral Cortex* 4:576-589, 1994). According to the methods described herein, these cells can be manipulated to provide a source of new neurons for diseased, injured, or otherwise damaged or malfunctioning CNS neurons in diverse regions of the brain and spinal cord.

A. Advantages of the Present Invention

As described further below, one of the techniques proposed for treating a neurological deficit involves removing neural precursors from a patient who has such a deficit and growing those cells in culture to generate large numbers of neural progenitors. The cells may then be re-implanted into the same patient using techniques known to those of ordinary skill in the art (e.g., see Stein et al., In: *Brain Repair*, pp. 87-103, Oxford University Press, New York, 1995, or Leavitt et al., *Soc. Neurosci. Abstr.* 22:505, 1996). Clearly, this technique is advantageous to those presently in use that require embryonic cells from aborted fetuses; it avoids altogether the ethical issues raised by the need to use aborted fetuses as tissue donors. In addition, it is more likely to succeed because it will not stimulate the immune response that is responsible for a high incidence of transplant rejection.

Stimulating proliferation and migration of neural precursors in vivo has additional advantages; in vivo stimulation reduces the extent and possibly the number of invasive neurosurgical procedures. No stem cell excision surgery would be performed and multiple plugs of transplanted cells, which are typically required with embryonic or cultured cell grafts, would not be necessary. Further, there would be no massive die-off of undifferentiated neural progenitor cells due to the transplantation procedure. Typically, with human fetal dopaminergic cell grafts, 90% to over 99% of the implanted cells die before they become established in the host brain (Freed et al., *Soc. Neurosci. Abstr.* 22:481.3, 1996).

Another advantage provided by the present invention is that neural progenitor cells would not be isolated from the host brain by scar tissue. Plugs of transplanted cells become encapsulated within an envelope of glyotic scar tissue and reactive astrocytes. In addition to the physical barrier of the dense glyotic tissue, reactive astocytes within the scar tissue release factors which inhibit neurite outgrowth (McKeon et al., 1995). Neural progenitors created in vivo are not isolated from the rest of the brain by scar tissue. The outgrowth of their neurites, therefore, would not be inhibited by a massive proliferation of reactive astrocytes. The directed migration provided for herein therefore allows selective repopulation (which may vary in extent) of specific injured regions of the CNS with large numbers of new cells without disturbing undamaged areas.

The techniques presented here also represent an advance over the single previous study of forebrain neural stem cells stimulated in vivo. In that study, adult rats received ICV infusions of EGF for six days and were followed for up to seven weeks post-infusion (Craig et al., *J. Neurosci.* 16:2649-2658, 1996). In the present study, TGFα was infused for fourteen days and followed for up to three months following the end of infusion. This difference is critical in that only in the present study did the cells of the periventricular expansion migrate en masse into the overlying striatum. The directed mass migration of neural progenitors into a selected target area represents a much preferred method to repopulate degenerated brain regions with new neurons.

One area of intense recent interest is the manipulation of neural stem cell differentiation. Both the final location and the neurochemical phenotypes of the cells once they have differentiated are of primary importance and are discussed further below.

When neural precursor cells were removed from adult rodent brains and differentiated in vitro, cells immunochemically identified as astrocytes, oligodendrocytes and neurons are seen (Reynolds and Weiss, *Science* 255:1707-1710, 1992; Reynolds et al., *J. Neurosci.* 12:4565-4574, 1992; Lois and Alvarez-Buylla, *Proc. Natl. Acad. Sci. USA* 90:2074-2077, 1993). Many of the cells identified as neurons were also immunoreactive for GABA and substance P, neurochemical markers for two cell types normally found in the striatum. Precursor cells explanted from the adult human brain also expressed neuronal markers and displayed electrophysiological properties associated with neurons (Kirschenbaum et al., *Cerebral Cortex* 4:576-589, 1994).

These experiments suggest that when cells of the striatal ridge spontaneously differentiate in vivo, many of them will become cells with phenotypes typical of striatal neurons. Some recent data suggests that their phenotypes can be altered by exposure to different combinations of neurotrophins (Lachyankar et al., *Soc. Neurosci. Abstr.* 22:394.7, 1996). Progenitor cells receiving different treatments expressed different neurochemical immunomarkers once they differentiated, including acetylcholinesterase, GABA, tyrosine hydroxylase (TH), and calbindin. The expression of TH was particularly interesting, since combined proliferation, migration and directed differentiation into dopamine cells could provide a novel method to replace striatal dopamine lost in Parkinson's disease (PD).

In PD patients, functionally significant numbers of new dopamine-producing striatal cells would aid in the reversal of motor deficits in a manner similar to transplants of aborted fetal midbrain tissue. In patients with Huntington's disease (HD), neural precursors would be stimulated to repopulate the striatum with new medium spiny GABAergic and other neurons lost to the disease. Some recent evidence from a different line of research indicates that reconstruction of the striatopallidal pathway itself might be possible. Conditionally immortalized neural progenitor cells transplanted into the striatum differentiated and sent processes from the striatum to the globus pallidus (Lundberg et al., 1996).

B. Neurological Deficits Amenable to Treatment

Because the invention rests on the discovery that multipotent precursor cells can be stimulated to divide and migrate through the brain, it can be used to treat neurological deficits caused by a wide variety of diseases, disorders, and injuries. These insults include, but are not limited to, the following (others of skill in the art may categorize differently the diseases and disorders listed below; however categorized, the neurological deficits with which they are associated are amenable to treatment according to the methods of the present invention).

1. Degenerative Diseases

Degenerative diseases that can be treated according to the methods of the invention include Alzheimer's disease (AD), Parkinson's disease (PD), Huntington's disease (HD), Pick's disease, progressive supranuclear palsy (PSP), striatonigral degeneration, cortico-basal degeneration, childhood disintegrative disorder, olivopontocerebellar atrophy (OPCA; including a heritable form), Leigh's disease, infantile necrotizing encephalomyelopathy, Hunter's disease, mucopolysaccharidosis, various leukodystrophies (such as Krabbe's disease, Pelizaeus-Merzbacher disease, and the like), amaurotic (familial) idiocy, Kuf's disease, Spielmayer-Vogt disease, Tay Sachs disease, Batten disease, Jansky-Bielschowsky disease, Reye's disease, cerebral ataxia, chronic alcoholism, beriberi, Hallervorden-Spatz syndrome, cerebellar degeneration, and the like.

2. Traumatic and Neurotoxic Injuries to the Central Nervous System

Traumatic and neurotoxic injuries that can be treated according to the methods of the invention include gunshot wounds, injuries caused by blunt force, injuries caused by penetration injuries (e.g., stab wounds), injuries caused in the course of a surgical procedure (e.g., to remove a tumor or abscess from the CNS or to treat epilepsy), poisoning (e.g., with MPTP or carbon monoxide), shaken-baby syndrome, adverse reactions to medication (including idiosyncratic reactions), drug overdose (e.g., from amphetamines), post-traumatic encephalopathy, and the like.

3. Ischemia

Any disruption of blood flow or oxygen delivery to the nervous system can injure or kill cells, including neurons and glial cells, therein. These injuries can be treated according to the methods of the present invention and include injuries caused by a stroke (including a global stroke (as may result from cardiac arrest, arrhythmia, or myocardial infarction) or a focal stroke (as may result from a thrombus, embolus, hemorrhage, or other arterial blockage)), anoxia, hypoxia, partial drowning, myoclonus, severe smoke inhalation, dystonias (including heritable dystonias), acquired hydrocephalus, and the like.

4. Developmental Disorders

Developmental disorders that can be treated according to the methods of the invention include schizophrenia, certain forms of severe mental retardation, cerebral palsy (whether caused by infection, anoxia, premature birth, blood type incompatibility: etc. and whether manifest as blindness, deafness, retardation, motor skill deficit, etc.), congenital hydrocephalus, metabolic disorders affecting the CNS, severe autism, Down Syndrome, LHRH/hypothalamic disorder, spina bifida, and the like.

5. Disorders Affecting Vision

Disorders affecting vision, particularly those caused by the loss or failure of retinal cells, can be treated according to the methods of the invention. These disorders include diabetic retinopathy, serious retinal detachment, retinal damage associated with glaucoma, traumatic injury to the retina, retinal vascular occlusion, macular degeneration, heritable retinal dystrophies, optic nerve atrophy, and other retinal degenerative diseases.

6. Injuries and Diseases of the Spinal Cord

Injuries to or diseases affecting the spinal cord can also be treated according to the methods of the invention. Such injuries or diseases include post-polio syndrome, amyotrophic lateral sclerosis, nonspecified spinal degeneration, traumatic injury (such as those caused by automobile or sporting accidents), including any injury that crushes, partially severs, completely severs, or otherwise adversely affects the function of cells in the spinal cord), injuries caused by surgery to the spinal cord (e.g., to remove a tumor), anterior horn cell disease, paralytic diseases, and the like.

7. Demyelinating or Autoimmune Disorders

Neurological deficits caused by demyelination or an autoimmune response can be treated according to the methods of the invention. Such deficits can be caused by multiple sclerosis, possibly lupus, and others.

8. Infectious or Inflammatory Diseases

Neurological deficits caused by an infection or inflammatory disease can be treated according to the methods of the invention. Infections or inflammatory diseases that can cause treatable deficits include Creutzfeldt-Jacob disease and other slow virus infectious diseases, AIDS encephalopathy, post-encephalitic Parkinsonism, viral encephalitis, bacterial meningitis and meningitis caused by other organisms, phlebitis and thrombophlebitis of intracranial venous sinuses, syphilitic Parkinsonism, tuberculosis of the CNS, and the like.

9. Miscellaneous

Those of ordinary skill in the art are well able to recognize neurological deficits, regardless of their cause, and to apply the methods of the present invention to treat patients who have such deficits. In addition to the conditions listed above, which are amenable to treatment with the methods described herein, neurological deficits can be caused by Lesch-Nyhan syndrome, myasthenia gravis, various dementias, numerous parasitic diseases, epilepsy, and the like. The methods of the invention can be readily applied to alleviate neurological deficits caused by these and other diseases, disorders, or injuries.

C. Polypeptides that Bind the EGF Receptor

1. The EGF Family

Polypeptides in the EGF family appear, in some ways, unrelated. For example, TGFα and EGF have only 30% structural homology (Marquardt et al., *Science* 223:1079-1082, 1984). However, they display similar binding kinetics for, and stimulate tyrosine-specific phosphorylation of, the $M_r$ 180, 000 EGF membrane receptor (Cohen et al., *J. Biol. Chem.* 255:4834-4842, 1980; Reynolds et al., *Nature* 292:259-262, 1981). The functional equivalence of the two growth factors is partly attributed to the same relative positioning of six cysteine residues, represented by "C" in the concensus sequence: $CX_7CX_{4,5}CX_{10}CXCX_8C$. These conserved residues impose similar disulfide bond-mediated structural constraints and, thus, a related three-dimensional structure (Twardzik et al., *Proc. Natl. Acad. Sci. USA* 82:5300-5304, 1985). Those of ordinary skill in the art are well able to compare any given amino acid sequence with the EGF-family concensus sequence to determine whether a polypeptide is likely to be functionally equivalent to EGF (and, if so, useful in practicing the methods of the present invention). (see, e.g., Blomquist et al., *Proc. Natl. Acad. Sci. USA* 81:7363-7367, 1984, for a description of a computer search that revealed a similar pattern of cysteine and glycine residues in EGF, TGFα, and the sequence of a 19 kDa early protein of vaccinia virus).

In addition to EGF, TGFα, and vaccinia growth factor (VGF), the EGF family is known to include amphiregulin (AR), betacellulin (BTC), epiregulin (ER), heparin-binding EGF-like growth factor (HB-EGF), schwannoma-derived growth factor (SDGF), HUS 19878, myxomavirus growth factor Shope fibroma virus growth factor, and teratocarcinoma-derived growth factor-1 (TDGF-1; also known as Cripto-1 (CR-1).

2. Methods for Determining EGF Receptor Binding

Those of ordinary skill in the art are readily able to determine whether any given polypeptide binds the EGF receptor. As used herein, the term "binds" refers to any specific interaction between a polypeptide and the EGF receptor that results in signal transduction sufficient to elicit a biological response, preferably a response that contributes to the reduction of a neurological deficit. Preferably, any given polypeptide useful in the methods of the present invention will bind the EGF receptor with an affinity that is equivalent to at least 50%, more preferably at least 70%, and most preferably at least 90% of the binding affinity of EGF itself (see Twardzik et al., supra, for a comparison of the biological activity of VGF, TGFα, and EGF in EGF receptor binding).

If guidance is required in performing an EGF receptor binding assay, those of skill in the art can consult any one of numerous publications describing a suitable procedure (the five publications on this topic that follow are hereby incorporated by reference in their entirety). For example, one could consult Cohen and Carpenter, *Proc. Natl. Acad. Sci. USA* 72:1317-1321, 1975) or, for a modification thereof, Twardzik et al., supra. Similarly, for review of the EGF receptor, including specific binding and sequence information, signalling, and receptor topology, one may consult, for example, McInnes and Sykes (*Biopolymers* 43:339-366, 1997) Boonstra et al., (*Cell Biol. Intl.* 19:413-430, 1995), or Gill (*Mol. Reprod. Dev.* 27:46-53, 1990).

D. Directed Migration

The examples below also provide evidence for successful directed migration of neural precursor cells, particularly in the adult rodent forebrain. The immunohistochemical and other techniques employed in the working examples below (and described at length therein), as well as comparable techniques routinely performed by those of ordinary skill in the art, can be used to characterize the effect of any infusion of growth factor or any other stimulus applied to direct cellular migration. Indeed, it is possible to trace the cells' migration in some detail (i.e., the number of cells, their size, shape, and position within the nervous system can be determined).

A variety of stimuli can be applied to cells in vivo to direct their migration en masse (the term "en masse," when used herein to describe cellular migration, refers to the movement of a population of cells in substantially the same direction for a sufficient period of time to be visualized as a mass (as, e.g., is apparent in FIGS. 9, 10, and 11)). Broadly, one can direct migration in one of two ways: (1) in a conducive manner, i.e., by applying a stimulus that positively attracts migrating cells (such as a chemoattractant, neurotropic factor, or a compound (e.g., TGFβ) that increases the expression of a cell adhesion molecule or extracellular matrix molecule (e.g., fibronectin, laminin, or a neural cell adhesion molecule)), or (2) in a permissive manner, i.e., by applying a stimulus that inhibits a signal that would otherwise inhibit migrating cells.

The stimuli that direct migration include disruption of the tissue in the target area (which may be the site where cells have been damaged, e.g., the striatum or substantia nigra, where dopaminergic cells are known to be lost in association with a number of debilitating neurodegenerative diseases; the cerebral cortex, where neurons and glia are lost following an ischemic episode caused by, e.g., a thrombus or embolus; or the spinal cord, where motor neurons are lost due to, e.g., a traumatic injury; or may be any site where cells make abnormal connections due to a developmental disorder). Alternatively, tissue may be disrupted in or along a path extending from the source of the neural progenitor cells to the desired endpoint of their migration.

The tissue may be disrupted by physical force (e.g., ablating or excising neurons, or severing one or more of the processes that extend from the neuronal cell bodies) or by applying a chemical substance such as a toxin or neurotoxin (e.g., ricin or 6-OHDA), a corrosive chemical (e.g., an acidic or basic solution), a compound that induces apoptosis (see, e.g., Leavitt et al., Soc. Neurosci. Abstr. 22:505, 1996), a compound that induces demyelination (see, e.g., Lachapelle et al., Soc. Neurosci. Abstr. 23:1689, 1997), or a compound capable of inhibiting the activity of the cell, e.g., an antisense oligonucleotide (such as an oligonucleotide that inhibits transcription of the gene encoding the cell's primary neurotransmitter), an antibody, or a polypeptide. Many such compounds are known to those of ordinary skill in the art and include compounds that bind to, but fail to activate, a receptor on the cell surface, such as the metabotropic receptors normally bound by glutamate. For example, in the studies described below, the effect of dopamine denervation with 6-OHDA (together with infusion of TGFα) on cellular migration is apparent.

Those of ordinary skill in the art are well able to direct cellular migration by applying any of the chemical substances described above to a targeted area of the nervous system, particularly given the remarkably clear and accurate images of a patient's brain and spinal cord that can now be generated with, e.g., magnetic resonance imaging or computed tomographic scans.

Moreover, it is apparent from the studies described below that altering one or more of the variables associated with application of a compound that directs migration (those variables including the nature, position, concentration, and duration of the application) can be altered to direct more precisely the migratory path the cells follow and to define the place at which they come to rest.

E. Differentiation Factors

While some neural precursor cells may spontaneously differentiate, given enough time, substantially greater benefit can be realized by controlling when and where differentiation takes place; exerting such control allows one to limit neural "repopulation" (which may be partial or complete, so long as it is sufficient to reduce a neurological deficit) to areas of the CNS in need thereof. Accordingly, various stimuli can be administered before, during, or after contacting neural progenitor cells with a polypeptide that binds the EGF receptor.

Broadly, the stimuli inducing differentiation can be "general" or "directed." A general differentiation stimulus is one that stimulates a cell to differentiate as it naturally would and is applied whenever a neurological deficit can be reduced by stimulating a cell to express its natural phenotype. For example, it is known in the art that cells from the striatal subependymal zone differentiate into GABAergic neurons upon exposure to general differentiation signals. Thus, stimulating these cells to differentiate by applying a general differentiation factor would reduce the neurological deficits associated with Huntington's Disease; in these patients, GABAergic medium spiny neurons are lost selectively.

Those of ordinary skill in the art are well able to apply the known means of stimulating general differentiation to stimulate differentiation of the proliferating and migrating cells of the present invention. For example, contacting cells with a retinoblastoma protein is known to cause them to exit the cell cycle, a requirement for differentiation (for a recent study, see, Slack et al., J. Cell Biol. 140:1497-1509, 1998) and contacting cells with a cell cycle associated kinase inhibitor, p21, can maintain cells in a post-mitotic (i.e., differentiated) state (Berger et al., Soc. Neurosci. Abstr. 22:505, 1996). Another stimulus that can be applied to stimulate differentiation in the context of the present methods is a cyclin D cell cycle regulator (Ouaghi et al., Soc. Neurosci. Abstr. 22:1706, 1996). Should one wish to stimulate differentiation of oligodendrocyte precursors, integrins may be applied (see, e.g., Buttery et al., Soc. Neurosci. Abstr. 22:1723, 1996). Brain-derived neurotrophic factor (BDNF) and retinoic acid (RA) are well known for their abilities to stimulate cellular differentiation (see, e.g., Ahmed et al., J. Neurosci. 15:5765-5778, 1995).

In the event neural precursor cells are cultured prior to directing migration, they may be transplanted into an area of the brain that is capable of influencing their differentiation. For example, a higher percentage of transplanted neural precursor cells differentiated into neurons when placed near the subventricular zone (up to 35%) compared to those transplanted to more lateral sites (where only 0-8% of the cells differentiated) (Catapano and Macklis, Soc. Neurosci. Abstr. 23:345, 1997). Similarly, transplanted cerebellar precursors express markers for hippocampal neurons when they are transplanted into the hippocampus (Vicario-Abejon et al., J. Neurosci. 15:6351-6363, 1995). Accordingly, one of ordinary skill in the art will appreciate that, as an alternative to contacting the progeny of proliferating neural progenitor cells with a compound that stimulates their differentiation, the invention can be practiced by transplanting cells in or sufficiently near a region of the brain that is capable of directing their differentiation.

A directed differentiation stimulus is one that stimulates a cell to differentiate, but with a phenotype that is different from the one it would naturally express. A directed differentiation factor would be applied whenever a neurological deficit could be reduced by stimulating a cell to express a non-natural phenotype. One such instance is in the case of Parkinson's disease, where differentiation of striatal cells into dopamine-producing cells could substitute for the loss of dopaminergic innervation from the substantia nigra. Similarly, one would aim to stimulate expression of a cholinergic phenotype in the septal region, where cells are selectively lost in Alzheimer's Disease; in spinal motor neurons, which are lost in amyotropic lateral sclerosis and following traumatic spinal injuries; and in oligodendrocytes, which are lost in demyelination disorders such as multiple sclerosis.

Factors from the GDNF/neurturin (TGFβ) family, which are derived from a glial cell line, may induce differentiation in neural cells (which is, moreover, enhanced by RA) (Hishiki et al., *Cancer Res.* 58:2158-2165), and GDNF stimulates motor neuron differentiation in rat ventral mesencephalic cultures. BDNF and ciliary neurotrophic factor (CNTF) also promote motor neuron differentiation (their effects appear to be additive or synergistic to the effects of GDNF) (Zurn et al., *J. Neurosci. Res.* 44:133-141, 1996). In addition, motor neuron differentiation can be induced by application of vitronectin, which is expressed in the ventral region of the neural tube (Martinez-Morales et al., *Development* 124:5139-5147) and by the protein encoded by sonic hedgehog (Tanabe et al., *Curr. Biol.* 5:651-658, 1995). A member of the sonic hedgehog family, Indian hedgehog, is expressed in developing and mature retina and promotes retinal progenitor proliferation and photoreceptor development (Levine et al., *J. Neurosci.* 17:6277-6288, 1997).

Cortical neural progenitors adopt a region-specific phenotype influenced by EGF, TGFα and the type of substrate upon which they are grown. EGF or TGFα doubled the percentage of limbic neurons derived from non-limbic-area precursors when they were plated on growth factor-deficient Matrigel™ or collagen type IV (Ferri et al., *Development* 121:1151-1160, 1995).

Insulin is known to affect differentiation of fetal neuron cell cultures, even more than IGF-1 (Abboud et al., *Soc. Neurosci. Abstr.* 23:1425, 1997). Basic fibroblast growth factor (bFGF) and neurotrophins can be used to direct the differentiation of hippocampal cells (Vicario-Abejon et al., *Neuron* 15:105-114, 1995).

In one embodiment, the methods of the invention can be applied to restore neural pathways that are lost to degenerative illness. For example, differentiated striatal GABAergic neurons can restore striatopallidal projections upon their differentiation. Those of ordinary skill in the art are well able to recognize numerous neural pathways that are amenable to reconstruction by the methods of the present invention.

F. Pharmaceutical Compositions

Polypeptides suitable for use in the present invention (i.e., those that bind the EGF receptor or stimulate differentiation, also referred to herein as "active compounds") can be incorporated into pharmaceutical compositions suitable for administration. Such compositions typically comprise one or more polypeptides and a "pharmaceutically acceptable carrier," a term which is intended to include any and all solvents, dispersion media, coatings, antibacterial agents, antifungal agents, isotonic and absorption delaying agents, and the like, that are compatible with pharmaceutical administration. The use of such media and agents is well known in the art. Except insofar as any conventional media or agent is incompatible with the active compound, use thereof in the compositions is contemplated.

Those of ordinary skill in the art appreciate the need to formulate pharmaceutical compositions for their intended route of administration (which may include parenteral, e.g., intravenous, intradermal, or intramuscular injection; oral administration; or direct application to the affected area). It is contemplated that the present methods will be carried out by applying polypeptides to neural precursors harvested from the brain and placed in culture or directly to the precursor cells in vivo (by, e.g., infusion through an injection cannula or shunt, or by implantation within a carrier, e.g., a biodegradable capsule) but other routes of administration, particularly parenteral (preferably intravenous) administration, are also within the scope of the invention.

Solutions or suspensions useful in the pharmaceutical compositions of the present invention (e.g., in a composition containing a polypeptide that binds the EGF receptor and a compound that stimulates the differentiation of neural precursors) can include: sterile diluents such as water, normal saline, fixed oils, polyethylene glycols, glycerine, propylene glycol, or other synthetic solvents; antibacterial or antifungal agents such as benzyl alcohol, parabens (e.g., methyl parabens), chlorobutanol, phenol, ascorbic acid, thimerosal, and the like; antioxidants such as ascorbic acid or sodium bisulfite; chelating agents such as EDTA; buffers such as acetates, citrates, or phosphates; and agents for the adjustment of tonicity such as sodium chloride or dextrose. pH can be adjusted with acids or bases, such as hydrochloric acid or sodium hydroxide.

Pharmaceutical compositions suitable for injection include sterile aqueous solutions (where the active compound is water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists (proper fluidity can be maintained, for example, by using coatings such as lecithin, by maintaining a certain particle size in the case of dispersion, and by including surfactants). The composition must be stable under the conditions of manufacture and storage and must be preserved against the contaminating action of microorganisms such as bacteria and fungi, as described above. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide that binds the EGF receptor) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active compound plus any additional desired ingredient from a previously sterile-filtered solution.

In one embodiment, the active compound is prepared with one or more carriers that will protect it against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparing such formulations will be apparent to those skilled in the art. The materials can also be obtained commercially, for example, from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate the compositions of the invention in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound, the particular therapeutic effect to be achieved, and the limitations inherent in the art of compounding such an active compound for the treatment of individuals.

In lieu of direct application of polypeptides that bind the EGF receptor or stimulate cellular differentiation, nucleic acid molecules encoding those polypeptides can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al., *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded, for example, in the brain or spinal cord. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

G. Treatment Regimes

By way of example (those of ordinary skill in the art are well able to extrapolate from one model (be it an in vitro or in vivo model) to another, progressing toward optimal dosages for human patients), for a rodent brain, the infusions to stimulate proliferation of neural precursor cells were continued for a period of at least two weeks. The result being a dramatic increase in the numbers of undifferentiated progenitor cells along the adjacent ventricle. The continuous TGFα infusion applied in the working examples below also supports radial cellular migration, but is not sufficient, by itself, to stimulate the massive radial migration observed in certain animals. The duration of any treatment performed according to the methods described herein can be varied according to the desired results. For example, in the working examples below, the cells greatly increased their numbers for more than a week prior to their mass migration away from the ventricle. Moreover, delayed migration was facilitated by denervation of the target region, either neurochemically or mechanically, and may also be facilitated pharmacologically by the concurrent infusion of factor(s) such as another neurotrophic factor, TGFβ, which increases the regional expression of cell adhesion molecules believed to underlie the radial migration (as described above). The pattern of migration and the final location of the ridge of migrating cells can be controlled by altering the location of the infusion.

Those of ordinary skill in the art are well able to determine the required dosage of a compound administered in the context of the present invention. Preferably, the dosage will range, whether infused or released from a time-release vesicle, from 1 to 100 ng/kg/day of the active compound or ingredient (e.g., TGFα or any of the factors described above); more preferably, 1 to 50 ng/kg/day; and most preferably, 1 to 10 ng/kg/day will be administered.

EXAMPLES

Example 1

Expression of TGFα and EGF Receptor mRNAS in the Normal Developing and Adult Nigrostriatal System As reviewed in the Detailed Description, mRNAs encoding EGF-family neurotrophic factors are developmentally regulated in the nigrostriatal system. In the studies described below, the expression of TGFα and EGF receptor mRNAs is examined in the normal developing and adult rodent system.

A. Animals and Tissue Preparation

Adult male adult and timed-pregnant female Sprague-Dawley rats (250-350 g) were obtained from Simonsen (Gilroy, Calif.). For these experiments and all others described herein, the animals were maintained in a temperature and humidity controlled vivarium. Use of the animals for all of the experimental procedures employed was approved by the University of California, Irvine, Animal Research Committee in accordance with National Institutes of Health guidelines.

Newborn (P0), postnatal day 1 (P1), and P4 animals were anesthetized by hypothermia and sacrificed by decapitation. P10, P21, and adult animals were sacrificed by decapitation. Their brains were quickly removed, frozen in isopentane at −20° C., and stored at −70° C. Coronal cryostat sections were cut at 20 μm and thaw-adhered to Vectabond™ (Vector Labs, Inc.) coated slides in ordered anterior-to-posterior rows. The sections were postfixed with 4% paraformaldehyde in 0.1 M phosphate buffer (pH 7.4) for 1 hour, rinsed in phosphate buffer and air dried. Sections were stored with desiccant at −20° C. until processed.

B. Hybridization Probes

TGFα mRNA probes were generated from a 550 nucleotide XbaI/BamHI cDNA fragment from the 5' end of rat TGFα and subcloned into pGEM 7Zf (Promega, Inc.). Antisense and sense probes were transcribed with SP6 and T7 polymerases, respectively. Rat EGF receptor mRNA probes were produced from a 718 base pair BamHI/SphI insert from the 5' end of the gene, in pGEM 7Zf. Probes for rat TH were created using the 1.2 kb BamHI/EcoRI fragment subcloned into pGEM 7Zf. Antisense subclones for EGF receptor and TH were transcribed with T7 polymerase. Sense subclones for EGF receptor and TH were transcribed with SP6 polymerase. All probes were radiolabeled by transcription in the presence of [$^{35}$S]UTP (NEN Research Products, Inc.).

C. In Situ Hybridization and Analysis

In situ nucleic acid hybridization was performed according to the method described by Simmons et al., (*J. Histotech.* 12:1169-181, 1989) except that developing brains were treated with 0.0001% proteinase K solution and 0.05 M EDTA. Sections were hybridized overnight at 65° C. with sense or antisense probes at a concentration of $10^7$ cpm/ml. Adjacent sections from the same animals were hybridized to each of the probes so that direct comparisons could be made of their anatomical distributions.

Slides from developing and adult animals were grouped together and apposed with $^{14}$C-labeled brain paste standards to autoradiographic BetaMax Hyperfilm (Amersham, Inc.) for six to seven days. After successful development of the autoradiography film, the slides were dipped in Kodak NTB-2 emulsion and exposed for four weeks. The autoradiographic sheet film and NTB-2 emulsion were developed with D-19 developer and Rapid Fix (Kodak, Inc.). The brain sections were then counterstained with thionin and coverslipped. Dipped and stained sections were examined semi-quantitatively and photographed under bright and dark field microscopy.

Expression of TGFα and EGF receptor mRNAs in the nigrostriatal system was traced through selected time points from early postnatal development to adulthood. TGFα mRNA hybridization was found in abundance in the early postnatal striatum but was gradually reduced to near adult levels by P21. Expression in the corpus callosum increased through postnatal development to levels comparable to those in the striatum. TGFα mRNA was not detected in significant abundance in the developing or the adult substantia nigra.

Striatal EGF receptor mRNA peaked early in postnatal development and decreased again by P21. EGF receptor was highest in the neuroepithelia around the lateral ventricles, but was also found at moderate levels in the body of the striatum. In the developing ventral midbrain, EGF receptor mRNA was barely detectable in early postnatal brains, but gradually increased to moderate levels by P21.

In adult animals, TGFα mRNA expression was moderate in the striatum and low-to-moderate in the ventral striatum and nucleus accumbens. EGF receptor mRNA hybridization was found at low levels in the body of the striatum and nucleus accumbens with higher punctate expression dispersed throughout. It persisted at moderate levels in the regions of striatum immediately bordering the lateral ventricles.

In the adult ventral midbrain, EGF receptor mRNA hybridization was found in the substantia nigra (SN), particularly the medial pars compacta, and the paranigral and parabrachial nuclei of the ventral tegmental area (VTA).

Previous studies indicated that TGFα and EGF receptor mRNAs are strongly regulated during ontogeny of the nigrostriatal system and that their expression in the adult largely represents a continuation of the developmental pattern (Lazar and Blum, *J. Neurosci.* 12:1688-1697, 1992; Weickert and Blum, *Devel. Brain Res.* 86:203-216, 1995). TGFα and EGF receptor mRNA hybridization in the developing and adult animals closely paralleled the findings of these earlier reports. The persistence of their expression in the adult striatum and midbrain is consistent with a supportive role in the mature nigrostriatal system.

The moderate EGF receptor mRNA expression in the adult subependymal regions along the forebrain lateral ventricles suggests a role in the maintenance or function of cells in this region as well (Seroogy et al., *Brain Res.* 670:157-164, 1995; Weickert and Blum, 1995, supra). TGFα (or EGF) has been shown to support the survival and differentiation of "EGF-responsive" cells from this region when they are explanted and grown in vitro (Reynolds and Weiss, *Science* 255:1707-1710, 1992; Reynolds et al., *J. Neurosci.* 12:4565-4574, 1992). It may perform a similar function in vivo during development.

Example 2

Modulation of TGFα and EGF Receptor mRNA Expression by 6-hydroxydopamine Lesion and Striatal TGFα Infusion In situ hybridization was used to determine whether nigrostriatal TGFα or EGF receptor mRNA was altered by intrastriatal infusion of TGFα. In addition, the influence of unilateral 6-OHDA lesions on receptor expression in infused and uninfused animals was examined.

A. Treatment Groups

Adult male Sprague-Dawley rats weighing 250-300 grams were obtained from Simonsen (Gilroy, Calif.) and assigned to one of five treatment groups: (1) striatal TGFα infusion, nigral 6-OHDA lesion (hereafter, "lesion"); (2) TGFα infusion, no lesion; (3) artificial cerebrospinal (aCSF) infusion, lesion; (4) aCSF infusion, no lesion; (5) no infusion, no lesion. Four to eight animals were used per experimental group. The animals were monitored after each surgical procedure until fully recovered and maintained at all other times in a temperature and humidity controlled vivarium.

B. 6-Hydroxydopamine Lesions

Rats were anesthetized with 8 mg xylazine and 100 mg ketamine per kilogram body weight. A chilled solution of 4.8 mg/ml 6-hydroxydopamine HCl (6-OHDA; Sigma Chemical Co.) in 0.9% saline with 0.01% ascorbic acid was prepared immediately before injection. Using sterile technique, an 8 μl volume was stereotaxically injected into the left substantia nigra (+3.7 A/P; +2.1 M/L; +2.0 D/V) at a rate of 1 μl/minute using interaural zero as a reference (Paxinos and Watson, *The Rat Brain in Stereotaxic Coordinates*, Academic Press, San Diego, 1986). The success and extent of 6-OHDA lesions were monitored by tyrosine hydroxylase (TH) mRNA in situ hybridization in the midbrain. TH is the rate-limiting enzyme in the dopamine synthetic pathway and is a common marker for dopamine-producing neurons. One animal with an incomplete lesion (retaining significant numbers of nigral TH-IR cells) was excluded from the study and is not included in the total number of animals.

C. Infusions

Osmotic minipumps (model 2002, Alzet, Inc.) were implanted four to five weeks post-lesion. The minipumps were filled with approximately 200 μl of either 0.05 μg/ml TGFα in artificial cerebrospinal fluid (aCSF) for experimental animals, or aCSF only for control animals, and incubated overnight at 37° C. prior to implantation. Following anesthesia as above, and under sterile conditions, the 5 mm cannula attached to the minipump (brain infusion kit, Alzet, Inc.) was stereotaxically implanted into the left caudate-putamen (+1.2 A/P; +2.7 M/L) using Bregma as a reference (Paxinos and Watson, 1986, supra) and fixed to the skull with carboxylate cement (FIG. 1). The minipump itself was placed subcutaneously in the interscapular region. The infusate was delivered directly into the striatum over a period of two weeks at a rate of 0.5 μl/hour.

D. Tissue Preparation.

At the end of the infusion period, animals were sacrificed by decapitation. Their brains were quickly removed, frozen in isopentane at −20° C., and stored at −70° C. Coronal cryostat sections were cut at 20 μm and thaw-adhered to Vectabond™ (Vector Labs, Inc.) coated slides in ordered anterior-to-posterior rows. The sections were postfixed with 4% paraformaldehyde in 0.1 M phosphate buffer (pH 7.4) for one hour, rinsed in phosphate buffer and air dried. Sections were stored with desiccant at −20° C. until processed.

E. Hybridization Probes.

TGFα mRNA probes were generated from a 550 nucleotide XbaI/BamHI cDNA fragment from the 5' end of rat TGFα subcloned into pGEM 7Zf (Promega, Inc.). Antisense and sense probes were transcribed with SP6 and T7 polymerases, respectively. Rat EGF receptor mRNA probes were produced from a 718 base pair BamHI/SphI insert from the 5' end of the gene in pGEM 7Zf. Probes for rat TH were created using the 1.2 kb BamHI/EcoRI fragment subcloned into pGEM 7Zf. Antisense subclones for EGF receptor and TH were transcribed with T7 polymerase. Sense subclones for EGF receptor and TH were transcribed with SP6 polymerase. All probes were radiolabeled by transcription in the presence of [$^{35}$S]UTP (NEN Research Products, Inc.).

F. In Situ Hybridization.

In situ nucleic acid hybridization was performed according to the method described by Simmons et al. 1989, supra). Parallel sections from experimental and control animals were hybridized overnight at 65° C. with sense or antisense probes at a concentration of $10^7$ cpm/ml. Adjacent sections from the same animals were hybridized to each of the probes so that a direct comparison could be made of their anatomical distributions.

Slides from experimental and control animals were grouped together and apposed with $^{14}$C-labeled brain paste standards to autoradiographic BetaMax Hyperfilm™ (Amersham, Inc.) for three to seven days. After successful development of the autoradiography film, the slides were dipped in Kodak NTB-2 emulsion and exposed for four weeks. The autoradiographic sheet film and NTB-2 emulsion were developed with D-19 developer and Rapid Fix (Kodak, Inc.). The brain sections were then counterstained with thionin and coverslips were applied.

G. Analysis and Quantitation

Dipped and stained sections were examined and photographed under bright and dark field microscopy. Autoradiograms were analyzed quantitatively using an MCID system (Microcomputer Imaging Device, Imaging Research, Inc.). Densitometry readings were sampled at multiple sites within each anatomical region of interest and averaged. Relative concentrations of TGFα and EGF receptor hybridization were then estimated using a computer-generated third degree polynomial standard curve constructed from the $^{14}$C brain paste standards. The estimated values for each region in each treatment group were then averaged and their standard errors calculated. Brain regions ipsilateral to the experimental treatments were compared to the corresponding contralateral regions in the same sections or to corresponding regions in control brains at approximately the same positions. Significance of the comparisons was determined using the Student's t-test.

H. Normal Expression and Control Infusions

Figures 2A, 2B, 2C, 2D:
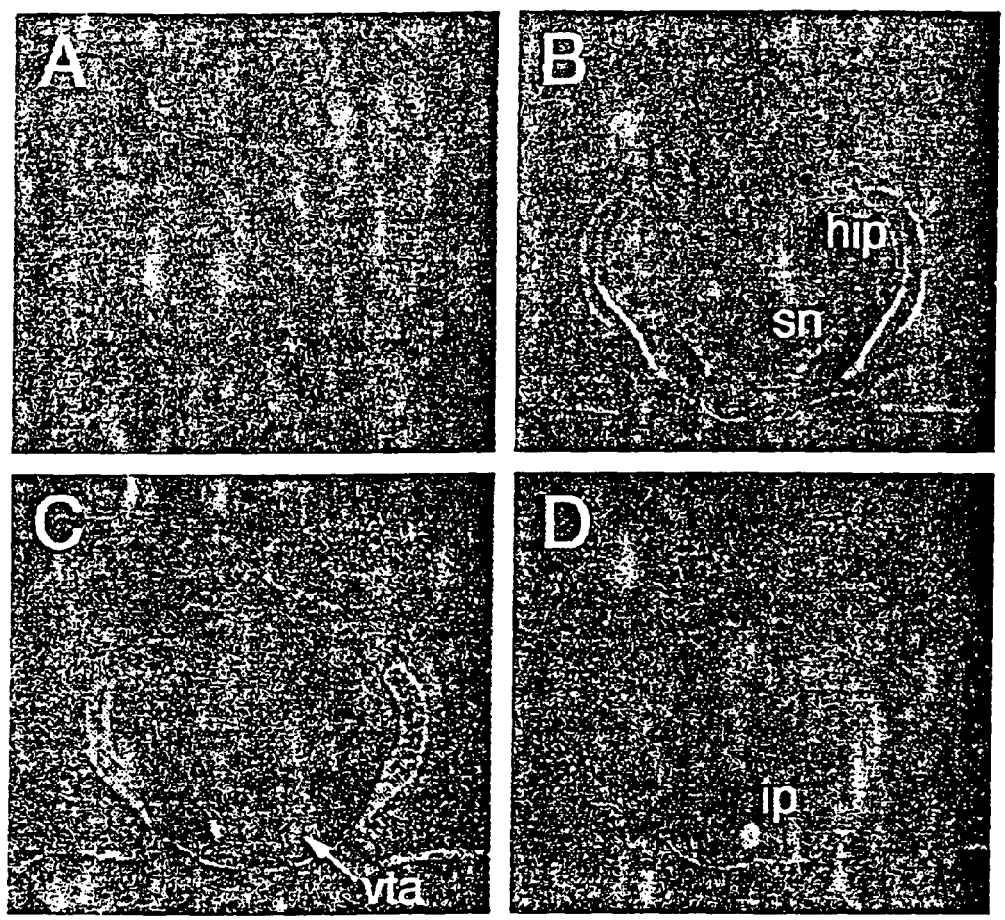
FIGS. 2A-2D are photomicrographs of coronal sections through the mesencephalon of the adult rat brain that have been probed to show the distribution of EGF receptor mRNA.
Figure 3:
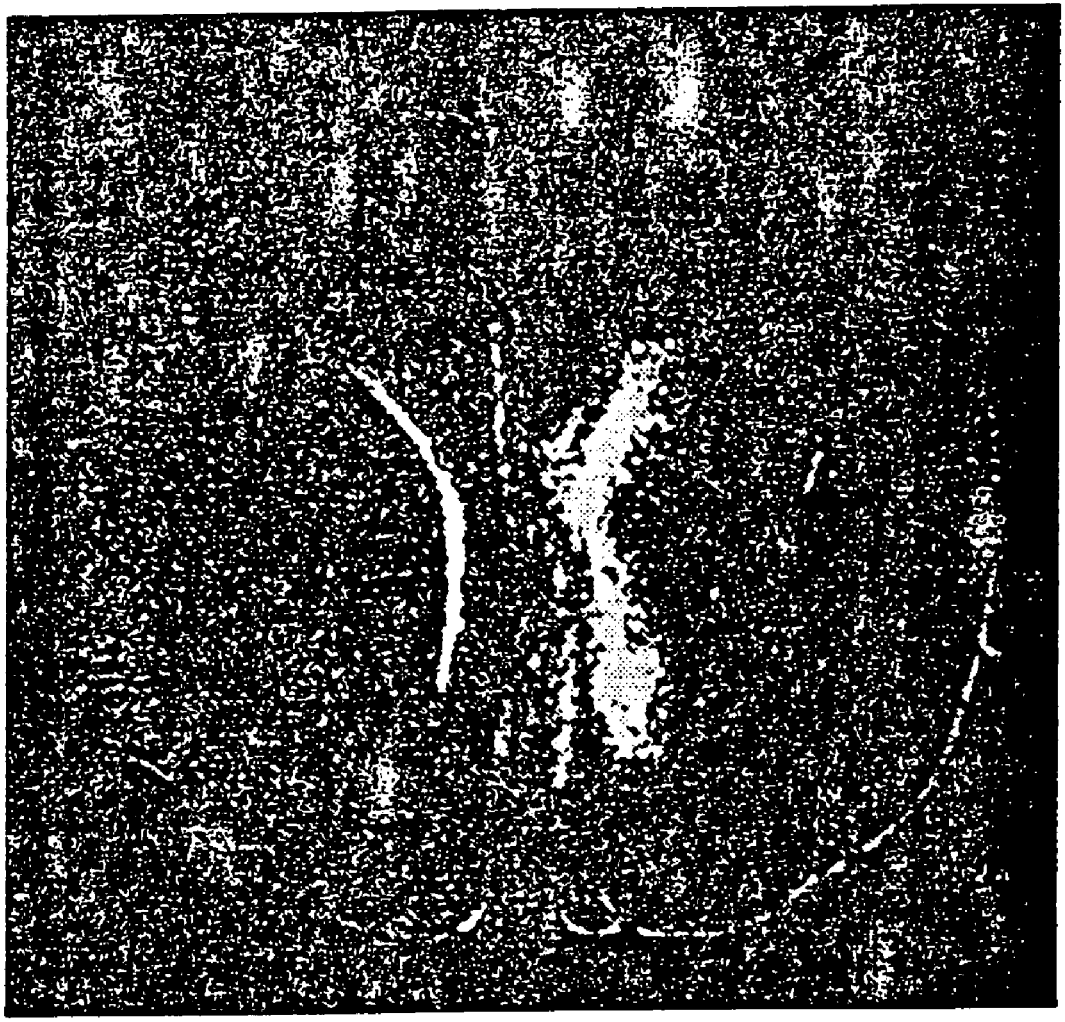
FIG. 3 is a photomicrograph of a coronal section through the striatum of an adult rat brain that was infused with TGFα and probed to show the distribution of EGF receptor mRNA. On the side of the infusion, a dramatic increase in hybridization density is apparent in the medial striatum adjacent to the lateral ventricle.

Expression of TH, TGFα and EGF receptor mRNAs in the striatum, the striatal subependymal region, and the SN in control animals receiving striatal infusions of aCSF was indistinguishable from that in normal animals (See Example 1 for normal developing and adult expression). TH mRNA hybridization was prominent throughout the SN-VTA. TGFα mRNA was not detected in the SN. EGF receptor mRNA, however, was prominent in the medial substantia nigra pars compacts (SNc), the paranigral, parabranchial, and interpeduncular nuclei of the VTA (FIG. 2).

TGFα mRNA hybridization was expressed in the caudate-putamen and nucleus accumbens (NA), being slightly less dense in the NA. EGF receptor hybridization was found at low levels throughout the body of the striatum and NA with higher punctate expression dispersed throughout the low level background, and at moderate levels in the proliferative regions of striatum bordering the lateral ventricles.

I. Effects of 6-OHDA Lesions

Figure 5:
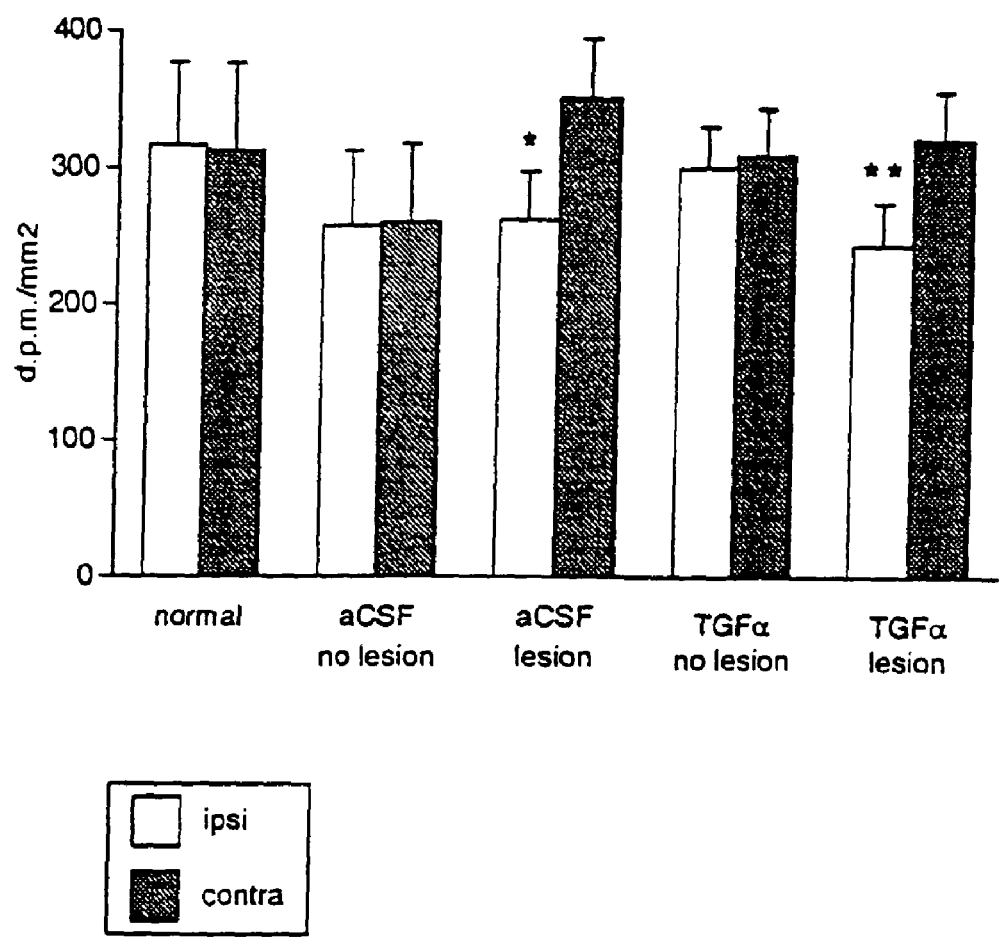
FIG. 5 is a bar graph showing the average standardized densities of TGFα mRNA hybridization in striata in each of five groups of animals examined (normal; aCSF infusion, no lesion; aCSF infusion, lesion; TGFα infusion, no lesion; TGFα infusion, lesion). The paired bars represent densities in striata ipsilateral and contralateral to the treatment. Average hybridization density was significantly reduced by one-quarter ipsilateral to the treatments in both groups receiving nigral 6-OHDA lesions. The striatal infusion of TGFα peptide had no impact on the decrease. Averages±S.E.M. (Student's t-test, paired for ipsilateral-contralateral comparisons; P values, * $p<0.005$, ** $p<0.001$).
Figure 6:
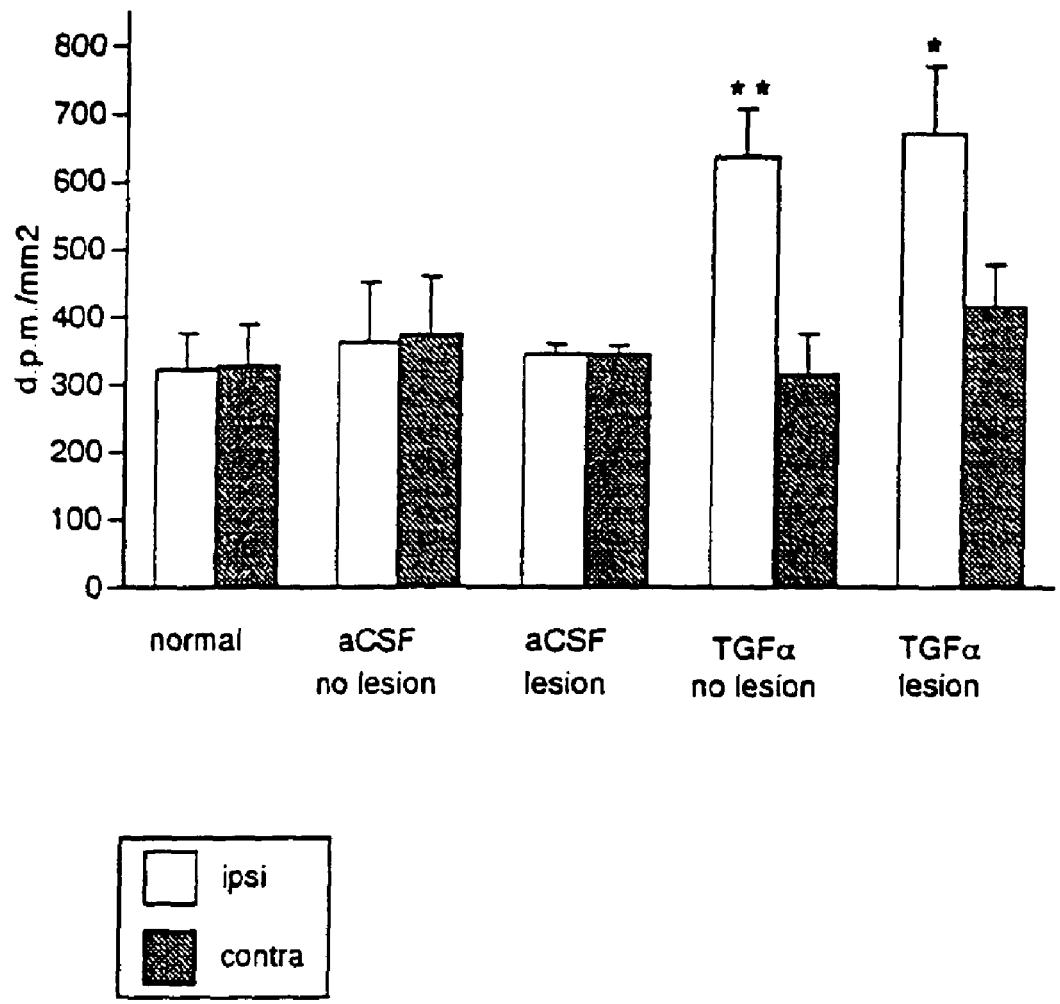
FIG. 6 is a bar graph showing the average standardized densities of EGF receptor mRNA hybridization in the subependymal regions along the edges of the striata bordering the lateral ventricles of animals in the same five test groups described in FIG. 5. The paired bars represent densities in striata ipsilateral and contralateral to the treatment. Average hybridization density was approximately doubled in the ipsilateral subependymal region in both groups receiving TGFα striatal infusions. Averages±S.E.M. (Student's t-test, paired for ipsilateral-contralateral comparisons; P values, * $p<0.01$, ** $p<0.0001$).

Unilateral nigral 6-OHDA lesions reduced TGFα mRNA hybridization in the ipsilateral striatum by 25%, but had no effect on contralateral TGFα mRNA hybridization (FIG. 5). Striatal and subependymal EGF receptor hybridization were unchanged in lesioned animals compared to normal animals (FIG. 6). In the midbrain, 6-OHDA lesions abolished EGF receptor hybridization in the ipsilateral SN-VTA.

J. Effects of TGFα Infusions.

In unlesioned animals receiving TGFα infusions, TGFα mRNA hybridization in the infused striatum was unchanged compared to the contralateral striatum or striata from normal animals (FIG. 5). A few of the animals receiving infusions of either TGFα or aCSF displayed a slight increase of TGFα mRNA hybridization immediately around the infusion cannula scar. TGFα mRNA hybridization in the substantia nigra was not increased to detectable levels by the infusions.

Hybridization to EGF receptor mRNA was dramatically increased in the ipsilateral subependymal region, but not in the rest of the striatum, in all animals receiving TGFα infusions (FIG. 6). No change from normal was observed in EGF receptor hybridization in the SNc with TGFα infusion alone.

K. Combined TGFα Infusion and 6-OHDA Lesion.

Striatal TGFα mRNA hybridization in animals receiving both striatal TGFα infusions and subsequent nigral 6-OHDA lesions was indistinguishable from that in lesion-only animals (FIG. 5). Similarly, EGF receptor hybridization in the midbrains of TGFα-infused/6-OHDA-lesioned animals was indistinguishable from that in lesion-only animals.

Figure 4:
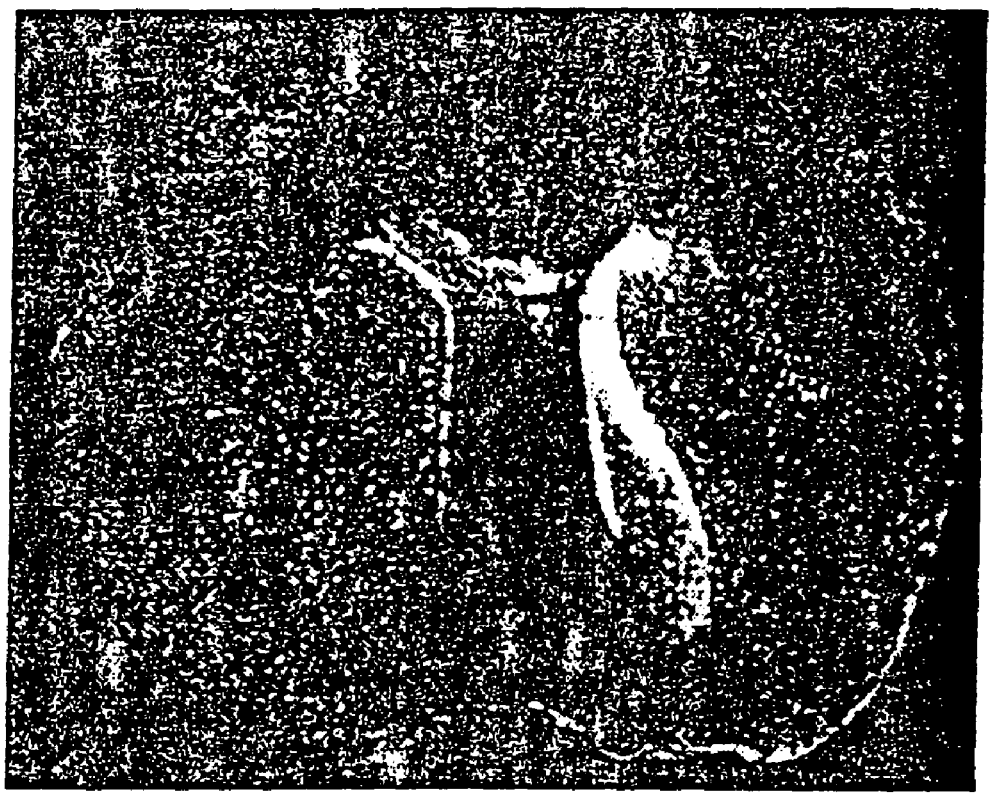
FIG. 4 is a photomicrograph of a coronal section through the forebrain of an adult rat brain that was infused with TGFα and lesioned with 6-OHDA. In situ hybridization was performed to localize EGF receptor mRNA, which appears as an intense ridge extending well into the body of the striatum.
Figure 7:
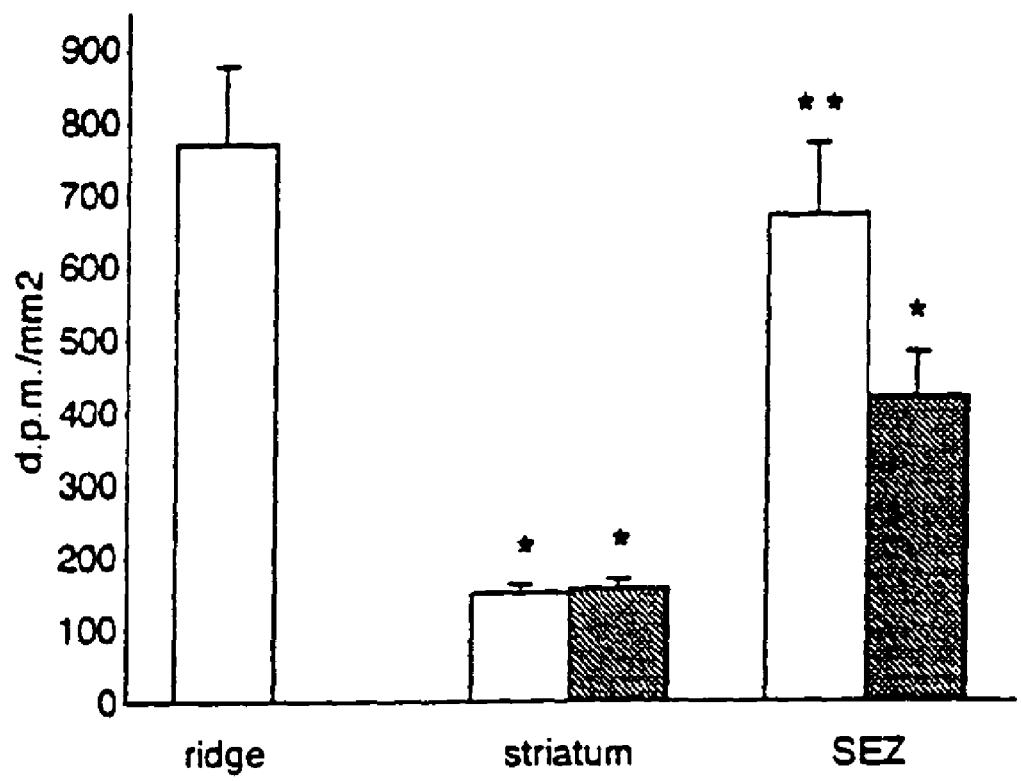
FIG. 7 is a bar graph showing the average standardized densities of EGF receptor mRNA hybridization in the striatal ridges, the non-ridge body of the striatum, and the subependymal regions in all animals with striatal ridges. The paired bars represent densities in striata ipsilateral and contralateral to the treatment. Average hybridization density was highest in the striatal ridge ipsilateral to the treatments. No striatal ridges ever appeared in the contralateral striata. TGFα striatal infusions. Averages±S.E.M. (Student's t-test, paired for ipsilateral-contralateral comparisons; P values, * $p<0.005$, ** $p<0.001$).
Figure 7:
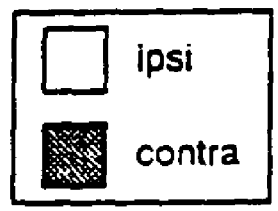

EGF receptor mRNA hybridization in the forebrain revealed an anomalous ridge of dense hybridization in the body of the ipsilateral striatum in addition to the increased hybridization in the subependymal region (FIGS. 4, 6, and 7). The ridge was found in five of the six rats in the combined TGFα infusion/lesion group, but only in one of six rats in the TGFα infusion/nonlesion group. EGF receptor hybridization in the surrounding striatum was unchanged.

L. Discussion

The results described above permit analysis of the modulatory effects of nigral 6-OHDA lesions or striatal infusions of TGFα, or both, on the expression of mRNAs encoding TGFα and the EGF receptor in the adult rodent nigrostriatal system. The results clearly demonstrated changes in expression associated with each treatment individually and a unique pattern of striatal expression when the two treatments were combined.

1. Effects of 6-OHDA Lesions

Midbrain lesions with 6-OHDA reduced TGFα mRNA hybridization in the striatum by 25% at several weeks post-lesion. If TGFα peptide levels parallel expression of TGFα mRNA in this system, the decrease in TGFα mRNA may be one aspect of the rodent lesion model that is not similar to idiopathic human PD: TGFα is greatly increased in the striata of PD patients (Mogi et al., *Neurosci. Lett.* 180:147-150, 1994). TGFα has been shown to enhance a number of measure of dopamine neuron function in vitro (Alexi and Hefti, *Neurosci.* 55:903-918, 1993). The increase of TGFα (and EGF and other trophic factors) may therefore reflect a response to the continuing degeneration of dopamine neurons and their striatal efferents and may contribute to the capacity of remaining midbrain dopamine cells to compensate for the lost striatal dopaminergic innervation (Mogi et al., 1994, supra). Thus, a partial- or perhaps a chronic-injury model might better represent this aspect of human PD.

The difference in the time course of the loss of dopamine cells may also help explain the apparent discrepancy between the 6-OHDA rodent model and human PD. In the rat model, midbrain dopamine neurons are killed relatively quickly by a single injection of neurotoxin. The chronic, progressive degeneration of mesencephalic dopamine neurons in human PD occurs over many years. In the present study, the animals were sacrificed well after midbrain dopamine cells had degenerated. There may have been early changes in striatal TGFα mRNA expression in these animals that would not be apparent in our experiments. It would be of interest to determine how TGFα mRNA expression varies in the rat model over shorter periods post-lesion, while dopamine neurons are in the process of degenerating.

Moderate TGFα mRNA expression in the caudate-putamen is consistent with its putative role as a target-derived growth factor for midbrain dopamine neurons. The underlying cause of its decrease in the ipsilateral striatum after midbrain neurotoxic lesion is unclear. Dopamine receptor binding has been shown to influence TGFα mRNA expression in the hypothalamus (Borgundvaag et al., *Endocrinol.* 130: 3453-3458, 1992), but no such interaction has yet been demonstrated in the striatum. TGFα mRNA is expressed in subpopulations of neurons and glia in the normal adult rodent striatum (Seroogy et al., *J. Neurochem.* 60:1777-1782, 1993). Dopamine denervation of the striatum could potentially have influenced TGFα mRNA expression in postsynaptic neurons, astrocytes or both.

Contralateral striatal TGFα mRNA expression was not significantly altered by 6-OHDA lesion. This finding, too, is consistent with a dopamine denervation-mediated decrease in TGFα mRNA expression. Only a few percent of mesostriatal dopaminergic projections are contralateral (Loughlin and Fallon, *Neurosci. Lett.* 32:11-16, 1982), thus any contralateral regulatory effects resulting from the lesion would be expected to be minor compared to ipsilateral effects.

EGF receptor mRNA hybridization in the DA-denervated striatum did not differ significantly from that in the contralateral CP or in unlesioned control striata. Again, there may have been early changes in expression due to the midbrain lesion or implantation of the infusion cannula that were not manifest at several weeks postlesion or two weeks post-implantation. The abolition of EGF receptor mRNA hybridization in the lesioned SNc confirms a similar observation after 6-OHDA lesion of the medial forebrain bundle (Seroogy et al., *Neuroreport* 6:105-108, 1994). This lesion-induced decrease was previously cited as evidence of EGF receptor expression by nigral dopamine neurons (Seroogy et al., 1994, supra), but the possibility remains of nigral glial production of EGF receptor mRNA that is subject to regulation by injury or death of nearby nigral dopamine neurons. Interestingly, EGF receptor binding in the midbrains of postmortem PD patients is unchanged from normals (Villares et al., *Brain Res.* 628:72-76, 1993). Thus, the loss of EGF receptor mRNA expression after lesion represents another difference between the rodent lesion model and human PD. As with TGFα expression in the striatum, a partial-lesion model may better mimic in a rat brain the changes seen in a Parkinsonian human brain.

2. Effects of TGFα Infusions.

In unlesioned animals, infusion of TGFα or aCSF did not significantly alter TGFα mRNA hybridization from normal levels in the midbrain or striatum. Despite reports of autostimulation of TGFα expression in other tissues or cell types (Coffey et al., *Nature* 328:817-820, 1987; Barnard et al., *J. Biol. Chem.* 269:22817-22822, 1994), results from the present study do not provide evidence for such activity in this system. The autostimulatory effects in those earlier studies were produced on the order of a few hours. Brain tissue in the present study was obtained after continuous exposure to the growth factor over a period of two weeks. Thus, an early upregulation near the beginning of the infusion that later subsided would not be evident.

As with TGFα and EGF receptor transcripts in lesion-only animals, it would be of interest to examine the time course of modulation at time points earlier after onset of the experimental treatment. The slight increase in TGFα mRNA seen in a few animals immediately around the infusion scar was found in both TGFα- and aCSF-infused striata. Thus, it is probably attributable to continued mechanical injury and gliosis caused by the cannula itself, and not to the infusate.

TGFα infusions dramatically increased EGF receptor mRNA hybridization in the ipsilateral subependymal zone but not in the rest of the striatum. In other tissues, EGF receptor mRNA can be modulated by several chemical and mechanical means. EGF peptide increased EGF receptor mRNA in numerous mammalian cell types in vitro (Earp et al., *J. Biol. Chem.* 261:4777-4780, 1986; Kesavan et al., *Oncogene* 5:483-488, 1990). Retinoic acid caused a similar increase in normal rodent fibroblasts (Thompson and Rosner, *J. Biol. Chem.* 264:3230-3234, 1989) and in a transformed rat liver cell line (Raymond et al., *Cell. Growth Diff.* 1:393-399, 1990). Exposure to cycloheximide, by itself or with EGF, stimulated an increase in cultured human cytotrophoblasts and stabilized EGF receptor transcripts, thus providing a mechanism other than enhanced transcription to increase total abundance of EGF receptor mRNA (Kesavan et al., 1990, supra).

Transection of the sciatic nerve in rats brought about a graded increase in EGF receptor mRNA in the severed ends (Toma et al., *J. Neurosci.* 12:2504-2515, 1992). Treatment with protamine increased $^{125}$I-EGF binding and cell surface receptor number in mouse and human cell lines in vitro (Lokeshwar et al., *J. Biol. Chem.* 264:19318-19326, 1989). TGFα may mimic these actions and increase the production and/or longevity of EGF receptor transcripts in extant subependymal cells. It may also stimulate transcription in cells that do not normally express appreciable amounts of EGF receptor mRNA. Both of these effects could be readily investigated further in vivo with routine techniques known to those of ordinary skill in the art.

An additional possibility is that TGFα is stimulating proliferation of subependymal cells and increasing the total numbers of cells expressing EGF receptor mRNA. EGF and TGFα are potent mitogens for cultured "EGF responsive" cells explanted from the subependymal region (Reynolds and Weiss, 1992, *Science* 255:1707-1710). The strong inductive effect striatal TGFα infusion had on subependymal EGF receptor mRNA hybridization may indicate that proliferative cells in the intact brain respond similarly to these cell in vivo.

3. Combined TGFα Infusion and 6-OHDA Lesion.

In animals receiving combined lesions and TGFα infusions, striatal TGFα mRNA hybridization was indistinguishable from that in animals receiving combined lesions and aCSF infusions. Although TGFα has potent autostimulatory effects in other tissues, it did not significantly alter the reduction of striatal TGFα mRNA hybridization in the present study. The 6-OHDA-mediated loss of mesencephalic EGF receptor mRNA was similarly unaffected by TGFα infusion. In the latter case, the midbrain lesions were performed, and ipsilateral dopamine cells destroyed, weeks prior to the start of the infusion. Thus, the growth factor would not have had an opportunity to prevent their elimination.

There is some evidence that the dopamine cells themselves express EGF receptor mRNA (Seroogy et al., 1994, supra)

and that TGFα can moderate the loss of markers for striatal dopaminergic innervation if administered concurrently with the neurotoxin. Therefore, the time interval between the neurotoxic lesions and the administration of TGFα may explain why TGFα infusions had no impact on the abolition of midbrain EGF receptor mRNA.

In human Parkinsonian brains, mesencephalic EGF receptor binding is unchanged from that seen in the normal brain (Villares et al., 1993, supra). The huge increases in striatal TGFα (and other neurotrophic factors) with PD (Mogi et al., 1994, supra) may mask a reduction in the number of EGF receptor expressing dopamine cells by increasing the levels of expression in the remaining neurons. On the other hand, in vitro experiments suggest that many of the trophic effects of TGFα on mesencephalic dopamine neurons are mediated, at least partially, through glia (Alexi and Hefti, 1993, supra). TGFα may therefore act through paracrine (direct) and sequential (indirect) modes of transport to influence dopamine neurons.

The pattern of EGF receptor mRNA hybridization in the subependymal zone of TGFα-lesioned animals was similar to that seen in TGFα-nonlesioned animals. The most striking feature in the ipsilateral striata of these animals was a dense ridge of hybridization well out of the body of the striatum, more intense even that the enhanced hybridization in the subependymal zone. The ridge did not correspond to any known anatomical feature and was not evident with the TGFα or TH probes. EGF receptor mRNA hybridization in the non-ridge striatum was the same as in the striata of all other groups.

The neurotoxic damage from the 6-OHDA lesions and the mechanical injury from implantation of the infusion cannula may have stimulated proliferation and activation of glial cells. Previous studies have demonstrated gliosis and increased astrocytic EGF receptor expression as a result of injury (Nieto-Sampedro et al., Neurosci. Lett. 91:276-282, 1988; Fernaud-Espinoza et al., Glia 8:277-291, 1993). Further, TGFα may play a role in the reactivity of astrocytes (Junier et al., J. Neurosci. 14:4206-4216, 1994).

Another possibility is that proliferative cells of the subependymal region were drawn away from the ventricle and into the overlying striatum by the combined growth factor infusion and midbrain lesion. TGFα is a potent chemoattractant for diverse cell types (Reneker et al., Development 121: 1669-1680, 1995), but by itself was not sufficient in most animals to stimulate formation of the ridge. Formation of the cellular ridge may have been facilitated by the midbrain lesions. The origin and identity of these cells will be examined in the following example.

Example 3

Characterization of the Striatal Ridge

As described above, striatal infusions of TGFα, when combined with nigral 6-OHDA lesions, induce the formation of a dense ridge of cells in the body of the striatum that abundantly expresses EGF receptor mRNA but no more TGFα than the surrounding tissue. The ridge was comprised of a mass of densely packed cells, allowing its clear detection using simple thionin staining. The identity of the anomalous striatal ridge was not apparent, but three possibilities were considered.

Gliosis in response to injury is a feature of both traumatic and neurotoxic damage to brain tissue. Typically, both types of brain injury stimulate astrocytosis and infiltration of injured tissue by astrocytes and microglia (Fernaud-Espinoza et al., Glia 8:277-291, 1993). Astrocytes have been shown to express EGF receptor immunoreactivity, particularly in response to brain injury (Gomez-Pinilla et al., Brain Res. 438:385-390, 1988; Nieto-Sampedro et al., Neurosci. Lett. 91:276-282, 1988). In addition, TGF itself stimulates the proliferation of astrocytes (Alexi and Hefti, Neurosci. 55:903-918, 1993). Therefore, the possibility that the striatal ridge was a mass of glial cells responding to the combined neurotoxic and mechanical damage and infusion of the growth factor was considered.

A second potential source for the ridge was investigated that was related to the distinctive anatomy of the rodent striatum. The ridge did not correspond to any previously identified anatomical feature. In rodents, the caudate and putamen are not anatomically distinct structures. No anatomical or neurochemical markers have been identified thus far that distinguish between these two nuclei of the basal ganglia in rodents. However, during prenatal and early postnatal development, neurogenetic gradients within different regions of the developing striatum correspond to characteristic gradients in the caudate and putamen in animals where these nuclei are anatomically discrete (Bayer, Intl. J. Devel. Neurosci. 2:163-175, 1984). In rodents, new striatal neurons rostral to the decussation of the anterior commissure are added in a lateral-to-medial gradient such that the latest born neurons are those nearest the lateral ventricle. That same pattern is observed in the development of the caudate nucleus, suggesting that the anterior striatum in rodents is more of a "caudate-like" region. Caudal to the crossing of the anterior commissure, neurons are added in a medial-to-lateral gradient, similar to the developing putamen in animals where it is anatomically distinct. Thus, the posterior rodent striatum may be more "putamen-like". The possibility was considered that the striatal ridge, then, might represent a previously unrecognized border between these two regions of rat striatum that allowed a dense buildup of cells, perhaps due to some neurochemical difference.

A third possibility for the source of the striatal ridge was also examined. Explanted cells from the subependymal zones of the forebrain lateral ventricles of adult mammals have been found capable of proliferating and differentiating into new neurons and glia, particularly when cultured in the presence of EGF-family neurotrophic factors, including TGFα (Reynolds et al., J. Neurosci. 12:4565-4574, 1992; Morshead et al., Neuron 13:1071-1082, 1994). Recently, EGF or TGFα infused into the lateral ventricle stimulated proliferation of "EGF-responsive" stem and neural progenitor cells in the adult mouse brain (Craig et al., J. Neurosci. 16:2649-2658, 1996). A possibility for the source of the striatal ridges in the present studies was that the TGFα infusions stimulated similar proliferative activity in the brains of rats. Additionally, the possibility that the striatal ridges were mass migrations of proliferating neural progenitor cells derived from the subependymal regions was considered.

The experiments described below served to allow characterization of this anomalous striatal ridge using a variety of histochemical and immunohistochemical techniques. The origin of the ridge and the factors influencing its appearance were also investigated by examining the time course of its formation in the striatum and by altering the combinations of surgical and chemical treatments.

A. Experimental Protocols

Adult male Sprague-Dawley rats weighing 250-300 grams were used throughout the study. Twenty-four animals received standard midstriatal infusions of rat TGFα (0.5 μg/day; Sigma Chemical Co.). Another 26 rats received either artificial cerebrospinal fluid (aCSF) or no infusion. A subset of animals in the standard TGFα infusion group and the control group received stereotaxic 6-OHDA injections into the substantia nigra 48 hours after the infusions were begun. Animals used in this portion of the study were classified into six groups according to their infusion-lesion combination, as follows: TGFα infusion, lesion (n=13); TGFα infusion, no lesion (n=11); aCSF infusion, lesion (n=12); aCSF infusion, no lesion (n=9); no infusion, lesion (n=1); no infusion, no lesion (n=4).

Additional animals received TGFα infusions into other regions of striatum, the lateral ventricle, cerebral cortex, or the septum. Four more animals (two per group) received midstriatal TGFα infusions at one-half or one-tenth the standard dose. Also, two animals received midstriatal infusions of epidermal growth factor (EGF) instead of TGFα. The EGF administered in these rats was at the standard 0.5 μg/day dose. All of the animals in these extra groups were lesioned. Rats in all of the experiments were typically perfused one to 16 days postlesion (3-18 days of infusion). To determine whether the ridge would persist after the infusions ceased, the minipumps were removed from four animals with TGFα infusions at the end of two weeks, but these animals were not perfused until several days later. Brain sections were prepared and stained using various immunocytochemical and histochemical techniques.

B. TGFα Infusion

Rats were anesthetized with 8 mg xylazine and 100 mg ketamine/kg. Infusions of TGFα were provided up to 18 days by Alzet osmotic minipump (2002). The minipumps were filled to about 200 μl with either aCSF for control animals or 20 μg TGFα in 400 μl of aCSF (50 μg/ml) for experimental animals. Under sterile conditions, the infusion cannula was positioned to stereotaxic coordinates (+1.2 A/P; +2.7 M/L; −6.0 D/V) based on Bregma (Paxinos and Watson, *The Rat Brain in Stereotaxic Coordinates*, Academic Press, San Diego, 1986) and cemented to the top of the skull with dental cement. The infusate was delivered via cannula at approximately 0.5 μl/hour. Some additional control animals received infusions either into the lateral ventricle, the overlying cortex, or other areas.

C. Neurotoxic Lesion

Forty-eight hours after the minipump implant, rats were anesthetized as above. A chilled 4.8 mg/ml solution of 6-OHDA HCl was prepared immediately prior to injection. Using sterile technique, the neurotoxin was stereotaxically injected into the ipsilateral substantia nigra (+3.7 A/P; +2.1 M/L; +2.0 D/V) using interaural zero as a reference (Paxinos and Watson, 1986, supra). A 6-8 μl volume was injected at a rate of 1 μl/minute.

D. Tissue Preparation

Animals were perfused with 500 ml of 4% paraformaldehyde in 0.1 M phosphate buffered saline (PBS; pH 7.4) one to 16 days postlesion and their brains placed into 20% sucrose. The next day, the brains were frozen in isopentane at −20° C. Forty-micron coronal sections were then cut on a freezing microtome into 2% paraformaldehyde in 0.1 M PBS. Continuous sections were taken through the striatum and substantia nigra-VTA. Representative sections were taken through the rest of the brain.

E. Nissl Staining

Microtomed brain sections for Nissl staining were mounted onto gelatin-coated slides and allowed to dry overnight. They were then dehydrated and rehydrated through ethanol baths, and placed in Thionin solution for approximately four minutes. The sections were dehydrated through the series of ethanol baths, cleared in successive Histoclear washes, and coverslipped. Section were viewed under light microscopy and photographed with Technical Pan Film (Kodak, Inc.) at ISO 100 (HC-110 processing for six minutes).

F. Silver Staining

Degenerating fibers and cells of the ridge were labeled using a modification to the Nauta staining method, similar to Procedure I of Fink-Heimer (Giolli and Karamanlidis, In: *Neuroanatomical Research Techniques*, R. T. Robertson, Ed., pp. 211-240, Academic Press, New York, 1978). Briefly, free-floating sections were placed into 0.05% potassium permanganate prior to treatment with fresh 1% hydroquinone-1% oxalic acid. They were treated with successive uranyl nitrate/silver nitrate solutions of increasing concentration. After another rinse, the sections were reacted in ammoniacal silver, then in ethanol/citric acid/paraformaldehyde reducer, and finally in sodium thiosulfate. After staining, the sections were mounted on glass slides and allowed to dry on a slide dryer for 15 minutes. The sections were then dehydrated through successive ethanol washes of increasing concentration, defatted in three successive Histoclear washes, and coverslipped.

G. Immunohistochemistry

The quality and the extent of the nigral lesion were determined by the loss of TH-IR in the ipsilateral ventral midbrain. Antibodies against glial fibrillary acidic protein (GFAP), a marker for astrocytes, nestin, a marker for neural progenitor cells, and vimentin, a marker for radial glial cells, were employed in the neurochemical characterization of the ridge. Immunohistochemistry was performed on free-floating sections. Briefly, brain sections were washed in 0.1 M PBS or Tris buffered saline (TBS; 3×10 minutes) then incubated for 1 hour in blocking solution consisting of 3% normal goat serum in 0.1 M PBS or TBS with 250 μl Triton X-100. Next, they were incubated overnight at room temperature on a rotator with antibody solution diluted with blocking solution: rabbit anti-TH antiserum (1:500; Eugene Tech Intl., Inc.), rabbit anti-GFAP (1:6400; Dako Corp.), mouse monoclonal anti-vimentin (1:50; Sigma Chemical Co.), or with mouse anti-nestin supernatant (1:20; University of Iowa Hybridoma Bank).

The sections then were washed and incubated for 1 hour with biotinylated goat anti-rabbit antiserum (1:200; Vector Labs, Inc.) for TH or GFAP immunostaining, or biotinylated horse anti-mouse antiserum (Vector Labs, Inc.) for nestin or vimentin immunostaining, then washed and incubated in avidin-biotin complex (ABC Elite kit, Vector Labs, Inc.) for 1 hour. Localization of primary antibody binding was revealed using the diaminobenzidine (DAB) peroxidase technique. The sections were washed thoroughly and mounted on gelatin-subbed slides and allowed to dry overnight. Finally, the sections were dehydrated, cleared, and coverslipped as described above.

None of the animals used in the study displayed adverse effects from the minipump implants or lesion surgeries. All continued to take food and water through the course of the experiments. If the lesion, infusion, or both were not successful, the animals (n=6) were excluded from the initial experimental groups and examined separately. A successful lesion was defined as one that caused complete or near-complete elimination of ipsilateral nigral TH-IR. A successful striatal infusion was defined as one where the tip of infusion cannula was successfully fixed into the body of the striatum.

As with the in situ hybridization studies, all animals receiving intrastriatal TGFα infusions of six days or more displayed a dramatic buildup of cells along the ventricle ipsilateral to the infusion, visible with thionin staining. By comparison, the contralateral striatum showed no such increase, and was indistinguishable from that in aCSF-infused animals. EGF infusions in lesioned animals induced the cellular expansion along the ventricle, but did not induce formation of the striatal ridge. Lower doses of TGFα induced both the cellular expansion and ridge formation, but, qualitatively, the number of cells in each was decreased.

1. Effects of 6-OHDA Lesions

None of the lesioned animals receiving aCSF infusions showed any cellular expansion along the ipsilateral ventricle or any evidence of a striatal ridge. Lesioned animals infused with TGFα did uniformly exhibit the buildup of cells along the ventricle and typically displayed the striatal ridge. Nigral lesions dramatically increased the incidence of formation of the ridge compared to unlesioned animals (Table 1).

2. Morphology and Persistence of the Ridge

Midstriatal infusion resulted in a characteristic S-shaped ridge arising from the dorsomedial caudate-putamen, sweeping out into the striatum and looping back slightly toward the midline at its ventral end. The dorsal-most portion of the ridge was continuous with the build-up of cells in the subependymal region. Typically, thionin staining was most dense in the dorsal portion of the ridge paralleling the EGF receptor mRNA hybridization. The cellular ridge was generally found throughout most of the rostral-caudal extent of the striatum. The ridge was still prominent in the striatum three months after the TGFα infusion pump was removed.

| Infusate | Lesion | Number | Expansion |
|---|---|---|---|
| aCSF | no | 9 | 0% | 0% |
| aCSF | yes | 12 | 0% | 0% |
| TGFα | no | 11 | 100% | 27% |
| TGFα | yes | 13 | 100% | 92% |

3. GFAP Immunohistochemistry

Antiserum against glial fibrillary acidic protein (GFAP), a marker for astrocytes, failed to stain cells of the striatal ridge or the cellular expansion along the ventricle. Normal GFAP-IR astrocytic staining was found medial and lateral to the ridge, but was nearly excluded from the ridge itself.

4. Silver Staining

Figures 8A, 8B:
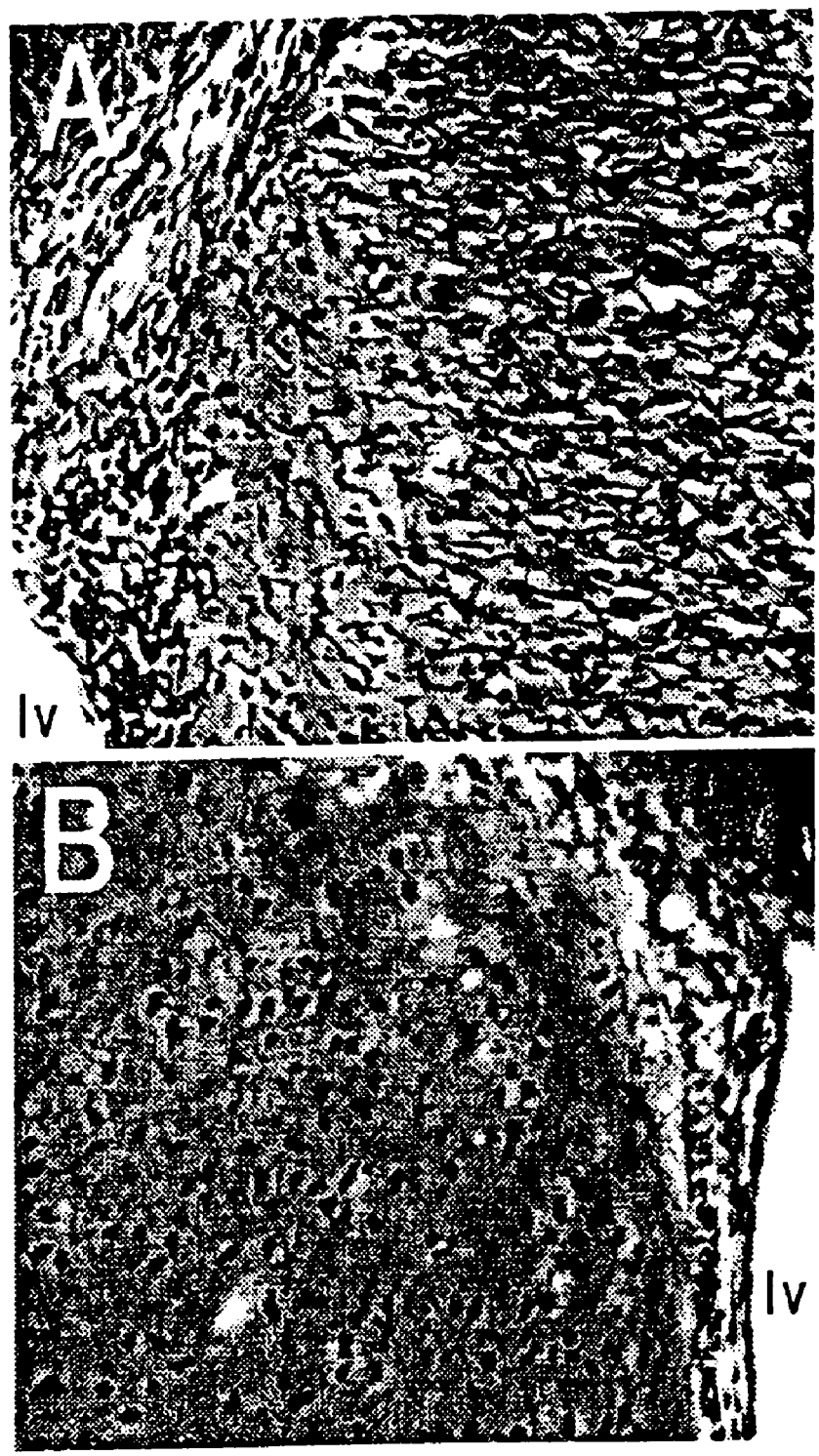
FIGS. 8A and 8B are photomicrographs of coronal sections through the striatum of an adult rat that received a nigral 6-OHDA lesion and TGFα infusion for fourteen days.

Labeling cells non-specifically with a modification of the Nauta method provided additional information about the cells comprising the ventricular cellular expansion and the striatal ridge. One of the most striking features was the huge number of cells making up the subependymal cellular buildup and ridge (FIG. 8). The cells were densely packed and predominantly fusiform in shape (FIG. 8). In the ventral portion of the ridge, elongated cells appeared to stream around fiber bundles of the internal capsule suggesting that the cells were migrating through the striatum.

5. Time Course of Ridge Formation

Figures 9A, 9B, 9C, 9D:
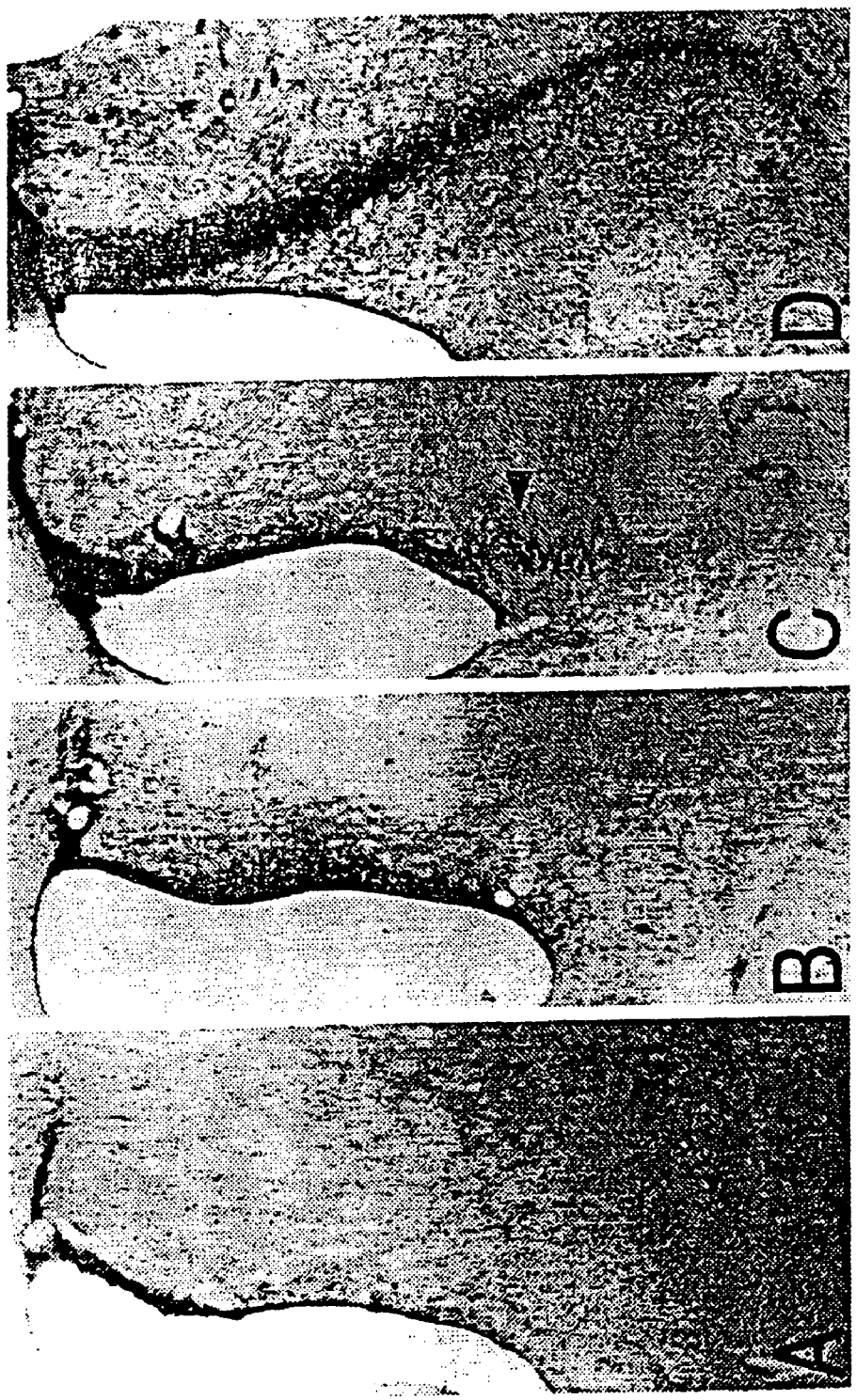
FIGS. 9A-9D are photomicrographs of thionin-stained coronal sections of adult rat brain from animals that were lesioned with 6-OHDA and infused with TGFα for variable periods of time.
Figures 10A, 10B:
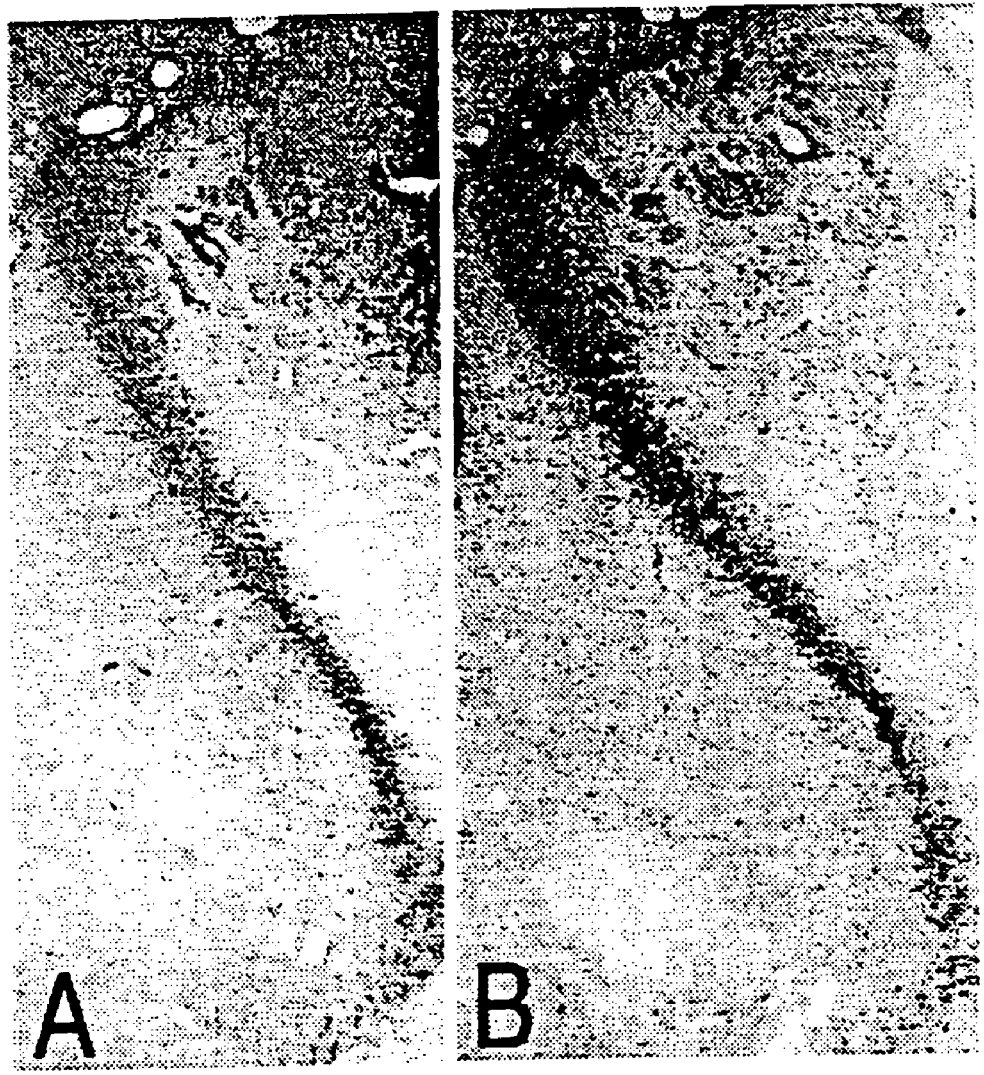
FIGS. 10A and 10B are photomicrographs of coronal sections of adult rat brain from animals that were lesioned with 6-OHDA and infused with TGFα for fourteen days.
Figures 11A, 11B, 11C:
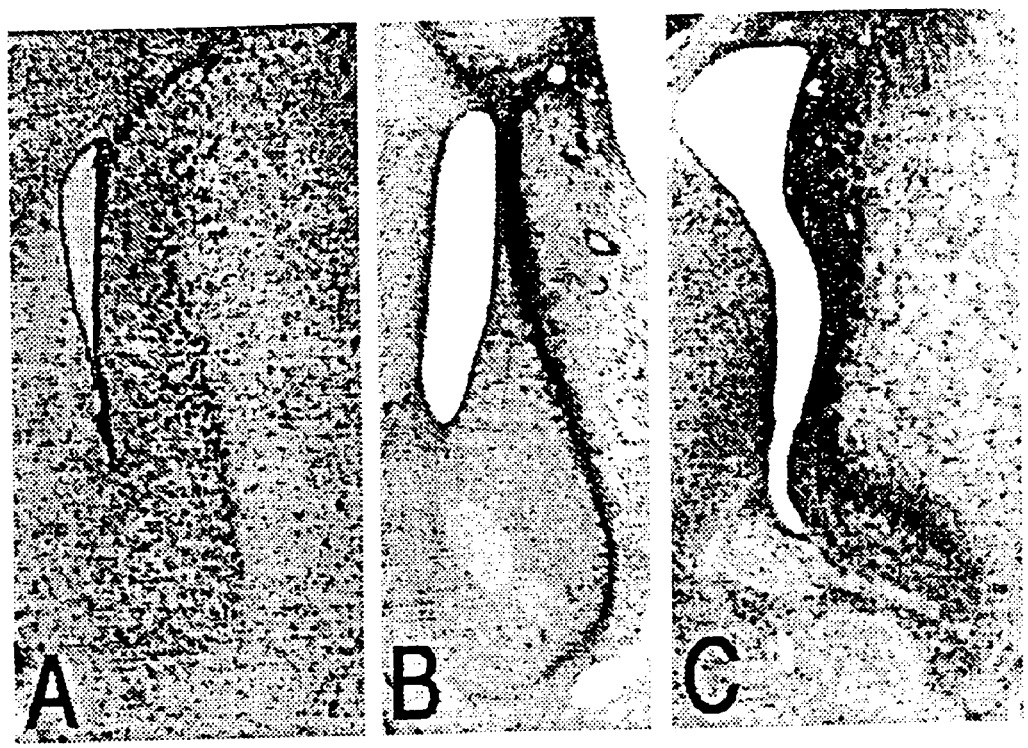
FIGS. 11A-11C are photomicrographs of thionin stained coronal sections from adult rat brain from animals that were lesioned with 6-OHDA and infused with TGFα, at varying distances from the lateral ventricle, for fourteen days. In FIG.

The density of cells of the ridge allowed us to track its formation using simple thionin staining (FIG. 9). All animals used for the time-course experiment received 6-OHDA lesions and midstriatal TGFα infusions. At time points prior to six days of infusion, there was only a very minor build-up of cells in the subependymal region and no evidence of a striatal ridge. By six days of infusion, there was a clear expansion of cells along the ventricle. At nine days infusion, the ventral portion of the ridge had begun to appear slightly displaced from the ventricle. By 12 days infusion, the ventral portion of the ridge was situated as much as 400 μm from the ventricle wall. At 16 days infusion, the ridge appeared midstriatum, its ventral portion up to two mm from the ventricle. Thus, the ridge originated in the ventricular region and was increasingly displaced radially in the overlying striatum at greater times of infusion. The estimated difference in distance between the lateral extents of the ridges and the ventricle wall at 12 days and 16 days of infusion was approximately 1.6 mm.

6. Nestin Immunohistochemistry

Monoclonal antibodies against nestin, a marker for neuroepithelial progenitor cells, intensely stained dense collections of fibers throughout the ridge (FIG. 10). No nestin-IR fibers were seen lateral to the ridge, but occasional fibers were observed medial to the ridge. The fibers were oriented primarily orthogonal to the ridge.

7. Alteration of Ridge Morphology

Lesioned animals infused midstriatally with TGFα uniformly exhibited a characteristic S-shaped striatal ridge in coronal sections. This morphology was dramatically altered in rats with infusions into other areas of the caudate-putamen (FIG. 11). Medial striatal infusions gave rise to an L-shaped ridge near the cannula infusion site with the vertical part of the "L" along the ventricle and the horizontal part extending orthogonally from the ventricle into the striatum. Infusion into the extreme lateral striatum stimulated the formation of a linear ridge parallel to the wall of the lateral ventricle.

8. Vimentin Immunohistochemistry

Antiserum recognizing vimentin, a marker for radial glial cells, failed to stain any cells in the striatum, the subependymal zone, or the striatal ridge at two weeks of infusion. However, this result is being investigated further, as the controls were performed in embryonic animals, under conditions that may not ensure elimination of false negatives.

9. Control of Ridge Position

Figure 12:
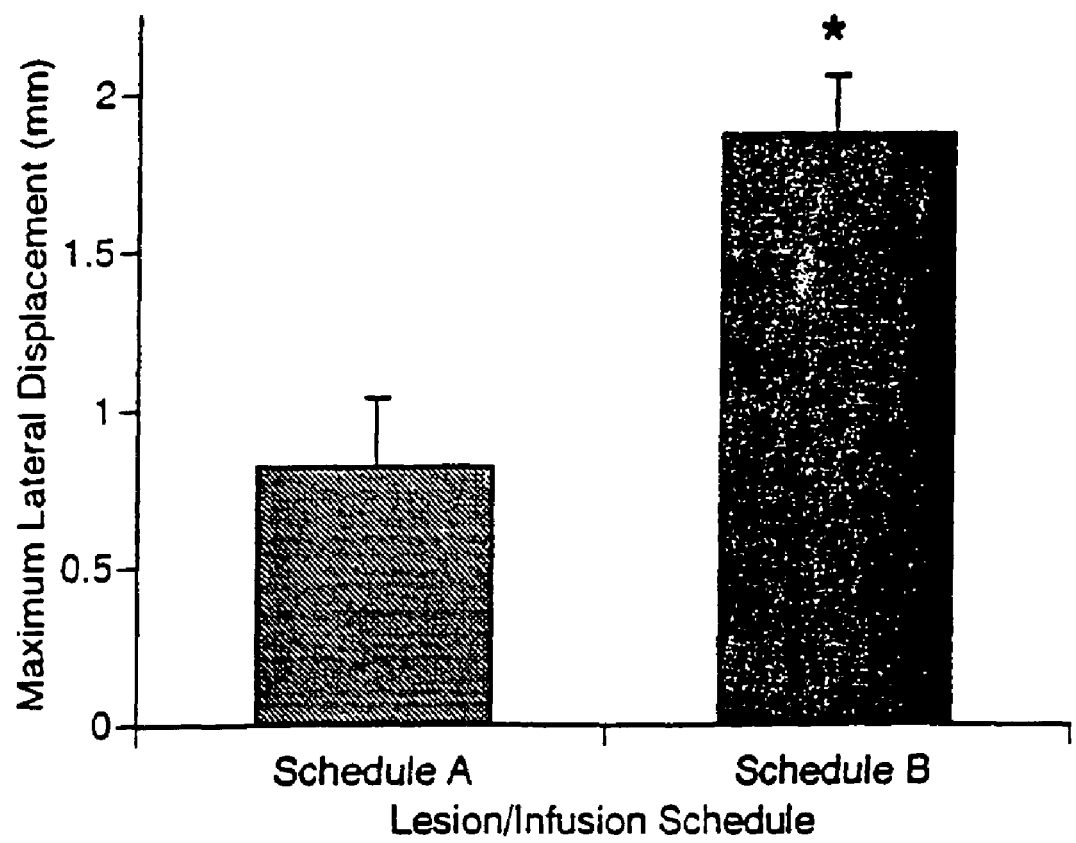
FIG. 12 is a bar graph depicting the maximum displacement of the striatal ridge (from the lateral ventrical; in mm) in coronal sections of adult rat brain after nigral lesion with 6-OHDA and mid-striatal infusion of TGFα for fourteen days. Animals treated according to "Schedule A" (left-most bar) received lesions first, followed by TGFα infusions four to five weeks later. Animals treated according to "Schedule B" received lesions two days after the 14-day TGFα infusion began. Averages±S.E.M. (Student's t-test; P value, * p<0.01).

Compared to the cells of ridges in rats used for in situ hybridization experiments, ridge cells in the present series of experiments were maximally displaced much farther from the ventricle (FIG. 12). The difference between these two groups of animals experimentally was the timetable of infusions and lesions.

Animals prepared for in situ hybridization experiments received lesions and then underwent a series of behavioral tests starting around the second week postlesion to confirm success of the unilateral lesions. Typically, those animals did not receive infusions until five weeks after the lesion. Thus, the dopamine degenerative process and the striatal infusion of TGFα were temporally separate events.

In the present series of experiments, infusions were begun first; lesions were not performed until 48 hours after the infusion pumps were implanted. In these animals, the degeneration of the nigral dopamine neurons, the resulting loss of striatal dopaminergic innervation, and the striatal administration of growth factor were temporally concurrent events.

10. Infusions into Brain Regions Other than the Striatum

All rats receiving infusions into brain areas other than the striatum received two-week TGFα infusions and nigral 6-OHDA lesions. Intracerebroventricular (ICV) infusion of growth factor ipsilateral to the lesion stimulated the buildup of cells in the adjacent ventricular wall, but did not induce formation of the striatal ridge in any of the animals.

Septal and some striatal infusions stimulated the formation of septal ridges associated with the medial walls of the lateral ventricles. Septal ridges, like the striatal ridges, were readily detected with EGF receptor mRNA in situ hybridization or with thionin staining, but tended to be qualitatively less robust in terms of the density and number of cells.

Dorsal cortical infusions, that is, infusions so shallow that they did not penetrate the corpus callosum, had no discernable effect on cell density along the lateral ventricle. Neither did these dorsal infusions induce formation of a ridge. Cortical infusions in which the corpus callosum was slightly penetrated stimulated expansion of cells along the ipsilateral ventricle, but did not induce formation of a striatal ridge. These animals did exhibit densities of cells in the corpus callosum that might be considered callosal ridges.

H. TGFα Stimulates Cellular Proliferation

The present experiments, together with those described above, demonstrate that TGFα administration was necessary for the formation of the cellular build-up and the striatal ridge. Not a single animal that received a striatal aCSF infusion—whether lesioned or not—displayed any obvious periventricular cellular expansion when compared to subependymal regions contralateral to the infusions or to normal animals. Clearly, cells of the forebrain are responding to striatal infusion of TGFα by proliferating along the lateral ventricle.

Recent studies with 6-day ICV infusions of EGF or TGFα in mice demonstrated a large increase in the number of cells around the ventricle immunolabeled with 5-bromo-2'-deoxyuridine (BrdU) or [$^3$H]thymidine, markers for cellular proliferation (Craig et al., *J. Neurosci.* 16:2649-2658, 1996). More than 95% of these cells were also positively immunoreactive for EGF receptor. Cresyl violet Nissl staining also showed an increase in the numbers of cells around the ventricles in these animals in response to growth factor administration.

The possibility that the expanded cell populations along the lateral ventricles were glial cells stimulated by the combined neurotoxic lesion and mechanical injury of the forebrain, and the infused TGFα was considered first. Astrocytes are known to respond to brain injury by proliferating and altering their morphology and functional properties (for review see Norenberg, *J. Neuropath. Exper. Neurol.* 53:213-220, 1994). Additionally, striatal astrocytes possess EGF receptors (Gómez-Pinilla et al., 1988, supra; Nieto-Sampedro et al., 1988, supra) and are stimulated by TGFα to proliferate (Alexi and Hefti, 1993, supra). In the present study, antiserum against glial fibrillary acidic peptide (GFAP), a marker for astrocytes, failed to demonstrate an increase in astrocytes in the ventricular region or in the ridge at two weeks of infusion. In fact, GFAP-IR was largely excluded from these areas. Normal astrocytic staining was seen medial and lateral to the ridge, for instance, but few GFAP-IR fibers were observed within the ridge itself. These findings paralleled those in experiments with six-day ICV infusions of EGF or TGFα: GFAP and an additional marker for astrocytes, S100β, showed no significant increase around the lateral ventricle (Craig et al., 1996, supra). Vimentin can also be expressed by reactive astrocytes (Federoff et al., *J. Neurosci. Res.* 12:14-27, 1984), but vimentin-IR was not observed in any of the sections examined. Markers for microglia (MAC-1) and oligodendrocytes (MAG, CNP, O4 and Rip) also did not change significantly (Craig et al., 1996, supra). Thus, the immunohistochemical evidence demonstrated that the TGFα-induced expansion of cells along the ventricle and in the striatal ridge were not the result of gliosis.

1. Cellular Morphology and Orientation

Silver and thionin staining clearly reveal the huge numbers of cells within the cellular aggregation along the ventricle. The cells were most dense and most numerous in the dorsal portions of the subependymal zone and ridge. The cells were predominantly fusiform, similar to migrating neural progenitor cells in the developing brain, with their long axes oriented orthogonal to the ventricle wall (or to the dorsolateral extension of the subependymal zone bordering the dorsal striatum). Silver stained cells in the ventral segment of the ridge appeared to stream around fiber bundles of the internal capsule, suggesting that they were migrating through the striatum.

To determine whether the cells were indeed migrating, a time course experiment was performed to examined the development of the ridge and its location as a function of time after the start of the growth factor infusion.

2. Migration of Cells of the Striatal Ridge

The progressive expansion of cells along the lateral ventricle and the subsequent radial movement of these cells as a dense ridge proved that the cells were indeed migrating en masse through the striatum. As such, the ridge could not have been an anatomical delineation between the rodent putative "caudate-like" and "putamen-like" regions of striatum.

3. Stimulation of Neural Precursor Cells

Although none of the immunomarkers for mature astrocytes, neurons, microglia, or oligodendrocytes labeled cells of the periventricular expansion or the striatal ridge, monoclonal antibodies recognizing nestin, an intermediate filament expressed by neuroepithelial precursor cells, intensely stained cell processes in the ridge and along the ventricle. Reactive astrocytes can also express nestin-IR, but the negative GFAP-IR in cells of the ridge eliminated the possibility that astrocytes formed a significant portion of the ridge cells. Nestin-IR has been used in recent years to identify and label neural precursor cells in vitro and in vivo (Lendahl et al., *Cell* 60:585-595, 1990; Craig et al., 1996, supra). The strong nestin-IR in the striatal ridge and the lack of immunostaining for glial markers support the conclusion that the cells of the ridge are predominantly neural progenitor cells.

Thus far, two distinct cell populations have been identified in adult mammalian brain that can give rise to new neurons and glia (Morshead et al., 1994, supra). One, the relatively quiescent cell population, are believed to be true multipotent neural stem cells. The other, the constitutively proliferating population, are believed to be neural progenitor cells, descendent from the stem cells. The stem cell population is thought to remain in the ependymal or subependymal zone and replenish the progenitor cell population as they die or migrate away. The term "neural precursor" is used here to describe any undifferentiated proliferative cell capable of giving rise to neurons and glia in the adult mammalian brain, whether these cells are neural stem cells or neural progenitors.

Previous studies have shown that many neural progenitor cells die in the subependymal zone before they can migrate from the region (Morshead and Van der Kooy, *J. Neurosci.* 12; 249-256, 1992). However, it was recently discovered that many others indeed survive and migrate along a highly-restricted path to the olfactory bulbs where they differentiate into olfactory interneurons (Luskin, *Neuron* 11:173-189, 1993; Lois and Alvarez-Buylla, *Science* 264:1145-1148, 1994). They migrate tangentially along the wall of the lateral ventricle in a process called "chain migration" wherein chains of migrating cells are ensheathed by specialized GFAP-IR astrocytes (Rousselot et al., 1994; Lois et al., *Science* 271:978-981, 1996).

The subependymal zone along the forebrain lateral ventricles, then, is much more than a dormant remnant of the embryonic neuroepithelium. In normal unmanipulated brains, it continues to give rise to new neuroblasts that migrate rostrally and differentiate into neurons. Under the influence of EGF-family neurotrophic factors, including TGFα, subependymal neural precursors can be stimulated in vitro to give rise to large numbers of new neurons, astrocytes and oligodendrocytes (Reynolds and Weiss, *Science* 255: 1707-1710, 1992). From these explant studies, it became clear that the highest concentrations of neural precursor cells were found in the dorsal portion of the subependymal zone, along the dorsal border of the caudate-putamen.

There is even some recent evidence that neural precursors may be stimulated to increase their numbers and produce new neurons and glia in vivo (Craig et al., 1996, supra). Cells double-labeled with BrdU and markers for mature neurons and glia were found diffusely distributed throughout the striatum, septum, and cortex after six days of ICV infusion of EGF and up to seven weeks of post-infusion survival. However, no mass migration of subependymal cells into the adjacent striatum was observed in that study (in marked contrast to the results obtained by the present method) and the numbers of cells were quite modest compared to the densely-packed mass of cells observed in the striatal ridge described herein. Moreover, none of the animals in Craig et al. received an infusion sufficient to stimulate the mass migration presently observed and none of the animals in that study received nigral 6-OHDA lesions, which are shown for the first time herein to dramatically increase the incidence of migration.

4. Evidence of Neuronal Phenotype

A question that remained was whether the cells within the massive expansion along the ventricle and the migrating striatal ridge truly were neural progenitor cells. Table 2 summarizes the data supporting the conclusion that these cells are indeed neural progenitors. The neurochemical evidence showed that they do not express markers for mature neurons, astrocytes, oligodendrocytes, or microglia. They did, however, intensely express a marker for immature neural progenitor cells. They expressed markers for cellular proliferation. They arose from the wall of the lateral ventricle where neural precursors are located in the adult rodent brain, expanded laterally and migrated radially away from the ventricle. Furthermore, their cellular morphology was fusiform and their processes were oriented orthogonal to the ventricle and the ridge, similar to migrating neural progenitors in the embryonic brain and consistent with their migration from the subependymal region. The data summarized in the following Table (Table 2) indicates that cells of the periventricular expansion and the striatal ridge are neural progenitors arising from subependymal neural stem cells.

Evidence of Progenitor Phenotype for Cells of the Expansion and Ridge

Neurochemical

Express abundant EGF receptor mRNA* and immunoreactivity
Immunonegative for GFAP* or S-100β markers for astrocytes
Immunonegative for NeuN, a marker for mature neurons
Immunonegative for MAG, CNP, 04, or Rip, markers for oligodendroctyes
Immunonegative for vimentin*, a marker for radial glia
Immunonegative for MAC-1, a marker for microglia
Immunopositive for nestin*, a marker for neuroepithelial precursors Morphological Elongated somata in ridge oriented orthogonal to subependymal zone
Nestin-IR processes in ridge oriented normal to subependymal zone Anatomical Arise from the subependymal zone
Highest density of cells is in the dorsal subependymal region Physiological Respond to TGFα administration by increasing their numbers 5. Mechanisms of Migration The mass migration of these cells into the striatum could be controlled by striatal dopamine denervation and by the location of the infusion cannula, but the mechanism of migration was unclear. The fact that the shape of the ridge could be modified simply by changing the site of infusion initially suggested a chemoattractant effect. TGFα is known to be a potent chemoattractive agent for diverse cell types (Ju et al., *J. Invest. Dermatol.* 100:628-632, 1993; Panagakos, *Biochem. Mol. Biol. Int.* 33:643-650, 1994). Its abundant expression in the perinatal caudate-putamen may indicate that it performs a similar role in the development of the striatum.

Neural precursor cells in the normal brain are located in a thin region in the wall of the lateral ventricle. Infusions into the mid-striatum were closer to cells of the dorsal end of this region. Presumably, cells migrating into the striatum would move toward putative higher concentrations of growth factor at the tip of the infusion cannula where the TGFα was released. The characteristic S-shape of ridges in animals with mid-striatal infusions might have resulted from receptor saturation of cells in the dorsal segment of the subependymal zone nearest the tip of the infusion cannula. Cells with saturated EGF receptors might have halted their migration once they moved close to the infusion site. Cells near the ventral end of the subependymal zone would see a lower putative growth factor concentration and would have to travel farther toward the infusion site before the concentration of TGFα increased enough to saturate their receptors. This differential migration with receptor saturation could explain the characteristic S-shape of these ridges.

Infusions into the medial striatum resulted in L-shaped ridges, again in keeping with a neurochemical gradient/receptor saturation effect. In this instance, dorsal subependymal cells may have had their receptors saturated and their migration halted before they could even emerge from the subependymal zone. Only cells in the most ventral portion of the subependymal region could migrate away from the ventricle.

Extreme lateral infusions essentially would have presented a similar putative concentration gradient to cells along most of the length of the proliferative region. The subependymal cells all migrated a similar distance from the ventricle, resulting in a roughly linear ridge, consistent with the idea of a chemoattractant, neurochemical gradient effect.

However, immunohistochemical evidence from the characterization studies cast doubt on the idea that a simple chemoattractant effect could entirely explain the mass radial migration. Nestin-IR processes of the migrating cells were not aligned with the tip of the infusion cannula, the region of the putative highest concentration of growth factor. Instead, they were oriented normal to the ventricle and the ridge. This orientation suggested that the cells migrated orthogonally into the caudate-putamen—as migrating neural progenitors do from the embryonic striatal neuroepithelium—not obliquely toward the tip of the infusion cannula.

Two additional findings discounted the role of simple chemoattraction in the migration of the ridge. First, the cells did not begin to migrate as they were produced; they increased their numbers along the ventricle for a period of more than a week, then migrated en masse as a dense sheet of cells. Further, lesion of the ipsilateral substantia nigra greatly increased the incidence of migration. Both of these observations suggested a more complex set of factors influencing the migration of the cells. These data did not entirely rule out a role for chemoattraction in the migration of the ridge, but they did indicate that a simple chemoattractive effect could not by itself account for it.

Another mechanism that might have contributed to the radial migration of neural progenitors in the adult striatum was the reconstruction of the radial glial scaffold due to the neurotoxic lesion, the mechanical injury done by the surgical implantation of the infusion cannula, or both. Radial glia guide the migration of neural progenitor cells in many regions of developing brain. They are anchored along the ventricle and extend their processes radially into the overlying parenchyma. They normally are transformed into GFAP-IR astrocytes in the early postnatal period once neuroblast migration is complete, and cease expression of vimentin and nestin.

Freezing injury of the cortical plate in neonatal rats inhibited radial glial transformation and caused the persistence of glial expression of vimentin and nestin in the injured regions of the adult brain (Rosen et al., *Dev. Brain Res.* 82:127-135, 1994). Kainate lesion of the adult rat hippocampus induced radial glial morphology and expression of nestin-IR and vimentin-IR in astrocytes of the hippocampal subependymal zone, suggesting that brain injury could stimulate a reversion of astrocytic phenotype to one found in the embryonic brain (Clarke et al., *Neuroreport* 5:1885-1888, 1994).

The present immunohistochemical experiments do not provide support for this phenomenon. Nestin-IR fibers were found in abundance in radially-oriented fibers along the ventricle at infusion day nine, but at later time points, they no longer remained along the ventricle. As the cells of the ridge migrated away from the subependymal region, so did the nestin-IR fibers. Furthermore, immunostaining for vimentin, a specific marker for radial glia, did not reveal any labeled fibers either in the ridge or in the subependymal region. Thus, it is unlikely that any astrocytes were reverted to their embryonic radial glial phenotypes or that astrocytic reversion played a role in the radial migration of the neural progenitor cells.

A newly-described mode of migration employed specifically by neural progenitors in the adult mammalian brain elucidates the tangential movement of these cells from the forebrain subependymal zones to the olfactory bulbs (Lois et al., 1996, supra). Rostrally migrating neuroblasts are densely packed and sheathed by GFAP-IR astrocytes bordering their highly-restricted migratory pathway. The migrating cells essentially form a solid stream of moving cells within a tube of specialized glial guide cells. The neural precursors in our experiments migrated as a sheet through the striatal neuropil—not along a restricted path—and were not associated with GFAP-IR cells. In fact, the proliferative subependymal zone and the cellular ridge largely excluded GFAP-IR. Thus, the mechanism of chain migration could not account for the radial migration seen in the present studies.

Another mechanism possibly underlying the mass neural progenitor migration was that cells of the striatum may have altered their expression of growth factors, cell adhesion molecules, or other substances in response to injury. In this scenario, the striatum may have been stimulated to provide its own chemoattractants or molecules that facilitate radial migration. Alternatively, it may also have been induced to downregulate expression of substances that inhibit migration.

Recent studies examining cell adhesion molecules in the striatum and subependymal region provide particularly intriguing insight. Highly polysialylated neural cell adhesion molecule (PSA-N-CAM) immunoreactivity is intensely expressed in the developing rodent striatum, but decreases as the animal matures (Aaron and Chesselet, *Neurosci.* 28:701-710, 1989; Szele et al., *Neurosci.* 60:133-144, 1994). PSA-N-CAM expression, however, persists along the adult forebrain subependymal region (Rousselot et al., 1994; Szele et al., 1994, supra). Partial decortication-induced striatal deafferentation dramatically increased expression of PSA-N-CAM and another adhesion molecule, L1, in the subependymal zone (Poltorak et al., *J. Neurosci.* 13:2217-2229, 1993; Szele and Chesselet, *J. Comp. Neurol.* 368:439-454, 1996). In the human brain, PSA-N-CAM expression is low in normal striatum, but is increased in the striata of Huntington's disease patients, particularly in the subependymal zone (Nihei and Kowall, *Ann. Neurol.* 31:59-63, 1992).

Of special interest were the changes occurring in fibronectin mRNA expression in the striatum after partial unilateral frontal decortication (Popa-Wagner et al., *Neuroreport* 3:853-856, 1992). Fibronectin is one of a number of molecules that have been shown to support neural migration in vitro (Fishman and Hatten, *J. Neurosci.* 13:3485-3495, 1993). Fibronectin mRNA hybridization was increased to a maximum level at 72 hours in the portion of the striatum immediately under the wound cavity. This early increase was interpreted as a component of the short-term wound healing process. Fibronectin expression in the greater ipsilateral striatum followed a longer-term increase, peaking at about ten days post lesion. This secondary increase was interpreted as the striatal response to deafferentation. Increases in expression of two other mRNAs that code for N-CAM and alpha tubulin followed only the early wound healing-related spatial and temporal patterns.

The ten-day peak of striatal fibronectin mRNA expression after deafferentation corresponds well to the delay of ridge migration following striatal dopamine denervation in the present studies. The delay of peak fibronectin mRNA expression may help explain why the progenitor cells of the invention did not begin to migrate radially until around the ninth day of infusion, and why, when they finally did migrate, they migrated en masse. In animals where the infusions and lesions were separated by several weeks, the maximum lateral migration distances at two weeks of infusion were dramatically reduced. This observation, too, is consistent with the transient peak in striatal fibronectin expression. In the few animals with ridges that did not also receive nigral lesions, mechanical injury of the overlying cortex may have stimulated enough fibronectin expression in the striatum to facilitate the migration. Fibronectin, then, may be upregulated in response to dopamine denervation of the ipsilateral striatum and, in turn, may temporarily facilitate radial migration of neural progenitors from the subependymal zone.

Another possible influence on radial migration of neural progenitors in the adult striatum may stem from a secondary effect by cell adhesion molecules. Infusion of N-CAM into the brains of adult rats receiving stab wounds to various areas of the brain, including striatum, inhibited astrocytic proliferation (Krushel et al., *Proc. Natl. Acad. Sci. USA* 92:4323-4327, 1995). Astrocytes release factors inhibiting neurite outgrowth and may thus inhibit neural regenerative responses. Thus, denervation of the striatum, and the associated increase in subependymal PSA-N-CAM may release inhibition of neural regeneration.

The enhancement of the migration effect in dopamine-denervated striatum may also have been related directly to the loss of dopaminergic innervation. During embryonic development of the striatum, immature neurons originate in the ventricular region and migrate radially (Bayer, 1984, supra; Bayer and Altman, *Prog. Neurobiol.* 29:57-106, 1987). The developmental migration of striatal neurons takes place prior to dopamine innervation by afferents from the midbrain. Stimulation of $D_2$ dopamine receptors on hypothalamic neurons dramatically attenuated TGFα mRNA expression and pituitary growth (Borgundvaag et al., *Endocrinology* 130:3453-3458, 1992). Although dopamine receptor-mediated inhibition of TGFα expression has not been studied in the subependymal zone, it is consistent with the depressed incidence of migration in non-lesioned animals. Thus, dopamine innervation during development may inhibit migration of striatal cells as the forebrain dopaminergic innervation becomes established.

Striatal dopamine may also contribute to the downregulation of striatal TGFα early in postnatal development as dopaminergic afferents become established. Dopamine denervation of the adult striatum may mimic for striatal cells some of the local chemical environmental cues normally only seen in the developing striatum—for instance, a reduction of available ligand for dopamine receptors expressed on striatal neurons. Striatal dopamine innervation has also been linked in a reciprocal manner to expression of extracellular matrix (ECM) molecules by astrocytes (Gates et al., *J. Chem. Neuroanat.* 6:179-189, 1993). Interestingly, TGFα is selectively elevated in the striata of PD patients (Mogi et al., *Neurosci. Lett.* 180:147-150, 1994) similar to the elevated expression in the embryonic striatum. If striatal TGFα is regulated by dopamine innervation, this increase may relate to the reduction of striatal dopamine and the consequent release of inhibition of TGFα expression.

Whatever the underlying mechanism, the time course experiment proved that subependymal cells could be stimulated to increase their numbers and migrate radially en masse into the adjacent striatum in the adult rat brain. Experiments in which the location or the dose of TGFα infusion was varied showed that movement of the striatal ridge and the gross numbers of cells involved could be controlled. The characterization experiments provided abundant evidence that the subependymal cellular expansion and the dense striatal ridge were composed of neural progenitor cells. The importance of these discoveries is discussed below, together with their potential application for the treatment of human neurodegenerative disease and traumatic brain injury.

The invention has now been explained with reference to specific examples and embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A method for treating an individual with a neurological disease selected from Alzheimer's disease or Huntington's disease or a neurological injury that results from ischemia, the method comprising intrastriatally administering to the individual a composition comprising a TGF-α polypeptide in a pharmaceutically acceptable carrier in a therapeutically effective amount, thereby ameliorating behavioral deficits that are attributable to the disease or injury.

2. The method of claim 1, wherein the ischemia is associated with a stroke.

3. A method for treating an individual suffering from central nervous system (CNS) damage or CNS lesion associated with Alzheimer's disease, Huntington's disease or ischemia, the method comprising intrastriatally administering to the individual a composition comprising a TGF-α polypeptide in a pharmaceutically acceptable carrier in a therapeutically effective amount, thereby ameliorating behavioral effects attributable to the CNS damage or CNS lesion.

4. A method for treating a neurological injury in an individual having a central nervous system (CNS) damage or CNS lesion associated with Parkinson's disease, Alzheimer's disease, Huntington's disease or ischemia, the method comprising intrastriatally administering to the individual a composition comprising a TGF-α polypeptide in a pharmaceutically acceptable carrier in a therapeutically effective amount, thereby ameliorating behavioral effects attributable to the neurological injury, wherein the administering of the composition is for a period of at least sixteen days.

5. A method for treating a neurological injury in an individual having central nervous system (CNS) injury associated with Parkinson's disease, Alzheimer's disease, Huntington's disease or ischemia, the method comprising intrastriatally administering to the individual a composition comprising a TGF-α polypeptide in a pharmaceutically acceptable carrier in a therapeutically effective amount, thereby ameliorating behavioral effects attributable to the neurological injury, wherein the administering of the composition is initiated four to five weeks after the occurrence of the injury.

6. The method of claim 4 or 5, wherein the administering is continuous.

7. The method of claim 4 or 5, wherein the CNS injury is associated with a stroke.

* * * * *